US010480035B2

(12) United States Patent
Parveen et al.

(10) Patent No.: US 10,480,035 B2
(45) Date of Patent: Nov. 19, 2019

(54) MULTIPLEX DIAGNOSTIC ASSAYS FOR LYME DISEASE AND OTHER TICK-BORNE DISEASES

(71) Applicant: Rutgers, The State University of New Jersey, New Brunswick, NJ (US)

(72) Inventors: Nikhat Parveen, West Orange, NJ (US); Salvatore A. Marras, Roselle Park, NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 307 days.

(21) Appl. No.: 15/021,317

(22) PCT Filed: Sep. 10, 2014

(86) PCT No.: PCT/US2014/054972
§ 371 (c)(1),
(2) Date: Mar. 11, 2016

(87) PCT Pub. No.: WO2015/038634
PCT Pub. Date: Mar. 19, 2015

(65) Prior Publication Data
US 2016/0289746 A1     Oct. 6, 2016

Related U.S. Application Data

(60) Provisional application No. 61/877,479, filed on Sep. 13, 2013.

(51) Int. Cl.
*C12Q 1/689* (2018.01)
*C12Q 1/6883* (2018.01)

(52) U.S. Cl.
CPC .......... *C12Q 1/689* (2013.01); *C12Q 1/6883* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | | |
|---|---|---|---|---|
| 2004/0029129 A1* | 2/2004 | Wang | .................. | C07K 14/195 435/6.18 |
| 2007/0020665 A1* | 1/2007 | Gupta | .................. | C12Q 1/6818 435/6.12 |
| 2010/0221718 A1 | 9/2010 | Hillebrand et al. | | |
| 2015/0238627 A1* | 8/2015 | Leger | .................. | C12N 15/113 514/20.9 |

OTHER PUBLICATIONS

Pietila et al., "Rapid Differentiation of Borrelia garinii from Borrelia afzelii and Borrelia burgdorferi Sensu Stricto by Light Cycler Fluorescence Melting Curve Analysis of a PCR Product of the recA Gene," Journal of Clinical Microbiology, Jul., vol. 38, No. 7, pp. 2756-2759 (Year: 2000).*
Park et al., "Rapid Identification of Candida dubliniensis Using a Species-Specific Molecular Beacon," Journal of Clinical Microbiology, August, vol. 38, No. 8, pp. 2829-2836. (Year: 2000).*
Huang et al., "Anaplasma phagocytophilum APH_1387 Is Expressed throughout Bacterial Intracellular Development and Localizes to the Pathogen-Occupied Vacuolar Membrane," Infections and Immunity, May, vol. 78, No. 5, pp. 1864-1873. (Year: 2010).*
GenBank Accession No. CR536516 [retrieved from: https://www.ncbi.nlm.nih.gov/nuccore/CR536516.1; retrieval date, Mar. 28, 2018, publicly available year (Oct. 2008).*
GenBank Accession No. FO082871 [retrieved on-line from: https://www.ncbi.nlm.nih.gov/nuccore/FO082871; retrieval date, Mar. 28, 2018].*
GenBank Accession No. U23457 [retrieved on-line from: https://www.ncbi.nlm.nih.gov/nuccore/U23457.1; retrieval date, Mar. 27, 2018, publicly available (1996).*
GenBank Accession No. DQ393401 [retrieved on-line from: https://www.ncbi.nlm.nih.gov/nuccore/DQ393401.1; retrieval date: Aug. 27, 2018] (Year: 2016).*
GenBank Accession No. DQ111056.1 [retrieved on-line from: https://www.ncbi.nlm.nih.gov/nuccore/DQ111056.1; retrieval date: Aug. 27, 2018] (Year: 2016).*
GenBank Accession No. JF331013.1 [retrieved on-line from: https://www.ncbi.nlm.nih.gov/nuccore/JF331013.1; retrieval date: Aug. 27, 2018] (Year: 2016).*
Saidac et al., "Detection and Quantification of Lyme Spirochetes Using Sensitive and Specific Molecular Beacon Probes," BMC Microbiology (Feb. 24, 2009); 9(43):1-10.
Pietila et al., "Rapid Differentiation of Borrelia garinii from Borrelia afzelii and Borrelia burgdorferi Sensu Stricto by LightCycler Fluorescence Melting Curve Analysis of a PCR Product of the recA Gene," Journal of Clinical Microbiology (Jul. 2000); 38(7):2756-2759.
Lodes et al., "Serodiagnosis of Human Granulocytic Ehrlichiosis by Using Novel Combinations of Immunoreactive Recombinant Proteins," Journal of Clincial Microbiology (Jul. 2001); 39(7):2466-2476.
Lin et al., "Global proteomic analysis of two tick-borne emerging zoonotic agents: Anaplasma phagocytophilum and Ehrlichia chaffeensis," Frontiers in Microbiology (Feb. 2011); vol. 2, Article 24, pp. 1-19.
Stuen et al., "Identification of Anaplasma phagocytophila (Formerly Ehrlichia phagocytophila) Variants in Blood from Sheep in Norway," J. Clin. Microbiol. (2002); 40(9):3192-3197.
Courtney et al., "Multiplex Real-Time PCR for Detection of Anaplasma phagocytophilum and Borrelia burgdorferi," Journal of Clincial Microbiology (Jul. 2004); 42(7):3164-3168.
Mommert et al., "Sensitive Detection fo Borrelia burgdorferi Sensu Lato DNA and Differentiation of *Borrelia* Species by LightCycler PCR," Journal of Clinical Microbiology (Jul. 2001); 39(7):2663-2667.

(Continued)

*Primary Examiner* — Young J Kim
(74) *Attorney, Agent, or Firm* — Fox Rothschild LLP

(57) ABSTRACT

The present invention provides novel methods of diagnosing and determining treatment strategies for Lyme disease and other tick-borne illnesses.

3 Claims, 7 Drawing Sheets

Specification includes a Sequence Listing.

(56) References Cited

OTHER PUBLICATIONS

Morrison et al., "Rapid and Sensitive Quantification of Borrelia burgdorferi—Infected Mouse Tissues by Continuous Fluorescent Monitoring of PCR," Journal of Clinical Microbiology (Apr. 1999);37(4):987-992.

Chan et al, "Sensitive multiplex PCR assay to differentiate Lyme spirochetes and emerging pathogens Anaplasma phagocytophilum and Babesia microti," BMC Microbiology (2013): 13:295 (1-15).

Dew-Jager et al., "The recA gene of Borrelia burgdorferi," Gene (Dec. 29, 1995); 167(1-2):137-40.

Cornillot et al., "Whole Genome Mapping and Re-Organization of the Nuclear and Mitochondrial Genomes of Babesia microti Isolates," PLOS One (Sep. 2013); 8(9):e72657, pp. 1-12.

Cornillot et al., "Sequencing of the smallest Apicomplexan genome from the human pathogen Babesia microti," Nucleic Acids Research (2012); 40(18):9102-9114.

Beyer et al., "The Anaplasma phagocytophilum effector AmpA hijacks host cell SUMOylation," Cellular Microbiology (2015); 17(4):504-519.

Casjens et al., "Whole-Genome Sequences of Two Borrelia afzelii and Two Borrelia garinii Lyme Disease Agent Isolates," Journal of Bacteriology (Dec. 2011); 193(24):6995-6996.

Schutzer et al., "Whole-Genome Sequences of Thirteen Isolates of Borrelia burgdorferi," Journal of Bacteriology (Feb. 2011); 193(4):1018-1020.

* cited by examiner

A.

B.

C.

SEQUENCE LISTING

<160> NUMBER OF SEQ ID NOS: 30

<210> SEQ ID NO 1
<211> LENGTH: 222
<212> TYPE: DNA
<213> ORGANISM: B. burgdorferi

<400> SEQUENCE: 1

```
gtggatctat tgtattagat gaggctctcg gcattggcgg atatcctagg gggcgcataa    60
tagaaatttt tggccccgag tcgtctggca agactacttt aactcttcaa gcgattgctg   120
aggtgcaaaa agaaggtggg atagctgctt ttattgatgc tgagcatgct cttgatcctg   180
tttatgcaaa agctttaggt gttaatgttg cagaactttg gc                      222
```

<210> SEQ ID NO 2
<211> LENGTH: 30
<212> TYPE: DNA
<213> ORGANISM: B. burgdorferi

<400> SEQUENCE: 2

```
ttatgcgccc cctaggatat ccgccaatgc                                     30
```

<210> SEQ ID NO 3
<211> LENGTH: 30
<212> TYPE: DNA
<213> ORGANISM: B. afzelii

<400> SEQUENCE: 3

```
ttatgcgccc cctaggatat ccaccaatgc                                     30
```

<210> SEQ ID NO 4
<211> LENGTH: 30
<212> TYPE: DNA
<213> ORGANISM: B. garinii

<400> SEQUENCE: 4

```
ttattcgccc cctaggatat ccaccaatgc                                     30
```

<210> SEQ ID NO 5
<211> LENGTH: 26
<212> TYPE: DNA
<213> ORGANISM: Artificial
<220> FEATURE:
<223> OTHER INFORMATION: Synthetic probe

<400> SEQUENCE: 5

```
ctggcggata tcctaggggg cgccag                                         26
```

<210> SEQ ID NO 6
<211> LENGTH: 104
<212> TYPE: DNA
<213> ORGANISM: Homo sapiens

<400> SEQUENCE: 6

```
agagcaagag aggtatcctg accctgaagt accctatcga gcacggcatc atcaccaact    60
gggatgacat ggagaagatc tggcaccaca ccttctacaa cgag                    104
```

<210> SEQ ID NO 7
<211> LENGTH: 287
<212> TYPE: DNA
<213> ORGANISM: B. burgdorferi

<400> SEQUENCE: 7

```
gcaagagttc aaatagaaaa agcttttgga aagggaagtc ttattaagat gggggaatct    60
cctgttggac aaggtataaa agtatgtca agtggatcta ttgtattaga tgaggctctc   120
ggcattggcg gatatcctag ggggcgcata atagaaattt ttggcccccga gtcgtctggc  180
```

```
aagactactt taactcttca agcgattgct gaggtgcaaa agaaggtgg gatagctgct        240 tttattgatg ctgagcatgc tcttgatcct gtttatgcaa aagcttt                    287
```

<210> SEQ ID NO 8
<211> LENGTH: 141
<212> TYPE: DNA
<213> ORGANISM: Artificial
<220> FEATURE:
<223> OTHER INFORMATION: Synthetic

<400> SEQUENCE: 8

```
tgagaggaac gaccatagcc ttttacatat gacacaagct ataactatag cagaaaatgg       60
aatttcggtg ttgttgacca gcggccgcga agaaggatgg ccaattttc caagacattt       120 ttcgtgtgat ttacctgatg g                                                141
```

<210> SEQ ID NO 9
<211> LENGTH: 152
<212> TYPE: DNA
<213> ORGANISM: Artificial
<220> FEATURE:
<223> OTHER INFORMATION: Synthetic

<400> SEQUENCE: 9

```
atggctacta cgaaggatgt gcttgtgaca aagatgccag cactaatgcg tactcgtatg       60
acaagtgtag ggtagtacgg ggaacgtgga gaccgagcga actggtttta tatgttggtg      120
atgagcatgt ggcatgtaga gatgttgctt cg                                    152
```

<210> SEQ ID NO 10
<211> LENGTH: 30
<212> TYPE: DNA
<213> ORGANISM: Artificial
<220> FEATURE:
<223> OTHER INFORMATION: Synthetic

<400> SEQUENCE: 10

```
gtggatctat tgtattagat gaggctctcg                                        30
```

<210> SEQ ID NO 11
<211> LENGTH: 30
<212> TYPE: DNA
<213> ORGANISM: Artificial
<220> FEATURE:
<223> OTHER INFORMATION: Synthetic

<400> SEQUENCE: 11

```
gccaaagttc tgcaacatta acacctaaag                                        30
```

<210> SEQ ID NO 12
<211> LENGTH: 20
<212> TYPE: DNA
<213> ORGANISM: Artificial
<220> FEATURE:
<223> OTHER INFORMATION: Synthetic

<400> SEQUENCE: 12

```
gcaagagttc aaatagaaaa                                                   20
```

<210> SEQ ID NO 13
<211> LENGTH: 19
<212> TYPE: DNA
<213> ORGANISM: Artificial
<220> FEATURE:
<223> OTHER INFORMATION: Synthetic

<400> SEQUENCE: 13
aaagcttttg cataaacag                                                    19

<210> SEQ ID NO 14
<211> LENGTH: 18
<212> TYPE: DNA
<213> ORGANISM: Artificial
<220> FEATURE:
<223> OTHER INFORMATION: Synthetic

<400> SEQUENCE: 14
tgagaggaac gaccatag                                                     18

<210> SEQ ID NO 15
<211> LENGTH: 22
<212> TYPE: DNA
<213> ORGANISM: Artificial
<220> FEATURE:
<223> OTHER INFORMATION: Synthetic

<400> SEQUENCE: 15
ccatcaggta aatcacacga aa                                                22

<210> SEQ ID NO 16
<211> LENGTH: 35
<212> TYPE: DNA
<213> ORGANISM: Artificial
<220> FEATURE:
<223> OTHER INFORMATION: Synthetic

<400> SEQUENCE: 16
cgcgtcggtg ttgttgacca gcggccgcgg acgcg                                  35

<210> SEQ ID NO 17
<211> LENGTH: 30
<212> TYPE: DNA
<213> ORGANISM: Artificial
<220> FEATURE:
<223> OTHER INFORMATION: Synthetic

<400> SEQUENCE: 17
ctttaggtgt taatgttgca gaactttggc                                        30

<210> SEQ ID NO 18
<211> LENGTH: 18
<212> TYPE: DNA
<213> ORGANISM: Artificial
<220> FEATURE:
<223> OTHER INFORMATION: Synthetic

<400> SEQUENCE: 18
atggctacta cgaaggat                                                     18

<210> SEQ ID NO 19
<211> LENGTH: 19
<212> TYPE: DNA
<213> ORGANISM: Artificial
<220> FEATURE:
<223> OTHER INFORMATION: Synthetic

<400> SEQUENCE: 19
cgaagcaaca tctctacat                                                    19

<210> SEQ ID NO 20

```
<211> LENGTH: 36
<212> TYPE: DNA
<213> ORGANISM: Artificial
<220> FEATURE:
<223> OTHER INFORMATION: Synthetic

<400> SEQUENCE: 20
cggtgcgaca aagatgccag cactaatgcg gcaccg                              36

<210> SEQ ID NO 21
<211> LENGTH: 18
<212> TYPE: DNA
<213> ORGANISM: Artificial
<220> FEATURE:
<223> OTHER INFORMATION: Synthetic

<400> SEQUENCE: 21
agagcaagag aggtatcc                                                  18

<210> SEQ ID NO 22
<211> LENGTH: 18
<212> TYPE: DNA
<213> ORGANISM: Artificial
<220> FEATURE:
<223> OTHER INFORMATION: Synthetic

<400> SEQUENCE: 22
ctcgttgtag aaggtgtg                                                  18

<210> SEQ ID NO 23
<211> LENGTH: 35
<212> TYPE: DNA
<213> ORGANISM: Artificial
<220> FEATURE:
<223> OTHER INFORMATION: Synthetic

<400> SEQUENCE: 23
cgctgcccta tcgagcacgg catcatcacg cagcg                               35

<210> SEQ ID NO 24
<211> LENGTH: 26
<212> TYPE: DNA
<213> ORGANISM: Artificial
<220> FEATURE:
<223> OTHER INFORMATION: Synthetic

<400> SEQUENCE: 24
aatattgttg aatggggata tttgtg                                         26

<210> SEQ ID NO 25
<211> LENGTH: 31
<212> TYPE: DNA
<213> ORGANISM: Artificial
<220> FEATURE:
<223> OTHER INFORMATION: Synthetic

<400> SEQUENCE: 25
aataatatag cttttccaaa atataactga c                                   31

<210> SEQ ID NO 26
<211> LENGTH: 29
<212> TYPE: DNA
<213> ORGANISM: Artificial
<220> FEATURE:
<223> OTHER INFORMATION: Synthetic

<400> SEQUENCE: 26
```

```
atgtatggta tagatataga gctaagtga                                                29

<210> SEQ ID NO 27
<211> LENGTH: 29
<212> TYPE: DNA
<213> ORGANISM: Artificial
<220> FEATURE:
<223> OTHER INFORMATION: Synthetic

<400> SEQUENCE: 27
ctaataactt agaacatctt catcgtcag                                                29

<210> SEQ ID NO 28
<211> LENGTH: 23
<212> TYPE: DNA
<213> ORGANISM: Artificial
<220> FEATURE:
<223> OTHER INFORMATION: Synthetic

<400> SEQUENCE: 28
cctatcgagc acggcatcat cac                                                      23

<210> SEQ ID NO 29
<211> LENGTH: 24
<212> TYPE: DNA
<213> ORGANISM: Artificial
<220> FEATURE:
<223> OTHER INFORMATION: Synthetic

<400> SEQUENCE: 29
gacaaagatg ccagcactaa tgcg                                                     24

<210> SEQ ID NO 30
<211> LENGTH: 20
<212> TYPE: DNA
<213> ORGANISM: Artificial
<220> FEATURE:
<223> OTHER INFORMATION: Synthetic

<400> SEQUENCE: 30
cgcgggggat cctataggcg                                                          20
```

MULTIPLEX DIAGNOSTIC ASSAYS FOR LYME DISEASE AND OTHER TICK-BORNE DISEASES

CROSS REFERENCE TO RELATED APPLICATIONS

This application is the U.S. National Phase of International Application No. PCT/US2014/054972, filed Sep. 10, 2014, which claims priority of U.S. Provisional Application No. 61/877,479 filed on Sep. 13, 2013. The content of these applications are incorporated herein by reference in their entirety.

GOVERNMENT INTERESTS

This invention was made with government support under grant number RO1 AI089921 from the National Institutes of Health. The United States government has certain rights to this invention.

FIELD OF THE INVENTION

The present invention relates to the diagnosis of Lyme disease and other tick-borne illnesses.

BACKGROUND OF THE INVENTION

Transmission of pathogens through tick vectors results in different infectious diseases in humans with Lyme disease affecting most people in the United States and Europe. Ticks can infect people with disease-causing organisms, including three different species of the Lyme spirochetes *Borrelia burgdorferi*, *B. afzelii*, and *B. garinii*, the intracellular bacterial pathogen *Anaplasma phagocytophilum*, and the protozoan *Babesia microti* and other *Babesia* species. Major species implicated in causing Lyme disease are *Borrelia burgdorferi* sensu stricto in the USA and additionally, *B. afzelii* and *B. garinii* in the European countries. Co-infection of *Borrelia* species with two other pathogens, *A. phagocytophilum* and *Babesia* species, has started appearing in both North America and Europe. *Babesia* species infect red blood cells (erythrocytes), cause babesiosis, and can also be transmitted through blood transfusion. Recently, several cases of vertical transmission of *B. microti* have also been reported. *A. phagocytophilum* infects polymorphonuclear leukocytes (PMNs), is an obligate intracellular pathogen and can cause lymphopenia/leukopenia and thrombocytopenia resulting in human granulocytic anaplasmosis (HGA). Both babesiosis and HGA can be fatal.

Currently, serological tests are used primarily to diagnose all three diseases with culture as the only available confirmatory test. However, assays that detect antibodies do not detect early infections (before antibodies are produced), and they cannot distinguish between active infections and infections that have been cured by treatment (as antibodies persist long after treatment is completed). Nucleic acid-based assays, on the other hand, are able to specifically detect the presence of the pathogens that cause Lyme disease and other tick-borne diseases. Yet, current assays that detect specific nucleic acid sequences are insufficiently multiplex to provide an accurate picture as to whether one or more of the infectious pathogens were introduced by the ticks during the bloodmeal. Furthermore, simultaneous infection with more than one pathogen can affect the sensitivity of currently available tests.

Sensitive diagnostic tests that can accurately diagnose Lyme disease, anaplasmosis and babesiosis are not currently available, thus, emphasizing a need to develop individual test for each pathogen or a combinatorial test for all three tick-borne pathogens to detect co-infection. Thus, there is a desperate need to develop a technically simple, rapid and accurate assay to unequivocally diagnose active disease caused by these three tick-borne infections, individually or together.

SUMMARY OF THE INVENTION

The invention addresses the above-mentioned need by providing agents and methods for diagnosing active disease caused by tick-borne infections.

In one aspect, the invention features multiplex primer-dependent assay methods, including particularly PCR assay methods, for detecting multiple genetic targets, including at least two of the following: a recA gene sequence of *Borrelia* that differs among *B. burgdorferi*, *B. afzelii*, and *B. garinii*; a BmTPK gene sequence of *B. microti* (conserved in other *Babesia* species that infect humans); and an APH 1387 gene sequence of *A. phagocytophilum*. The method includes providing a starting amplification reaction mixture that includes, in addition to a human or other mammalian sample suspected to contain at least one target sequence and amplification reagents (buffer, salts, dNTPs and DNA polymerase), and a primer pair and a molecular beacon probe for each intended target, wherein the primer pair defines an amplification product ("amplicon") that is 70-300 base pairs in length, and wherein each different molecular beacon probe is labeled with a spectrally distinguishable fluorescent or luminescent signaling moiety.

In a second aspect, the invention provides further sensitivity including amplifying each intended target sequence, if present, by the primer-dependent (for example, PCR) amplification process and detecting target-sequence amplicons with the molecular beacons, in real time, at end point, or by post-amplification thermal analysis of fluorescence versus temperature, including derivative curves. Assays according to this invention may be qualitative or quantitative. Preferred embodiments include homogeneous detection.

Methods according to this invention include the foregoing assays wherein the multiple genetic targets include a human genetic target as control, and wherein the starting amplification reaction mixture includes a primer pair and a molecular beacon probe for a human DNA gene sequence, and includes detecting amplicon from amplification of said human gene sequence. In such methods, a preferred human DNA sequence is a 70-300 base-pair region of the ACT A1 gene.

Certain preferred embodiments have as targets a BmTPK gene sequence of *B. microti*; and an APH 1387 gene sequence of *A. phagocytophilum*, with or without addition of a human gene target sequence.

Certain preferred embodiments have as a target a recA gene sequence of *Borrelia* that differs slightly among *B. burgdorferi*, *B. afzelii*, and *B. garinii*, plus at least one target that is a BmTPK gene sequence of *B. microti*; or an APH 1387 gene sequence of *A. phagocytophilum*, with or without addition of a human gene target sequence. For embodiments having a recA target sequence, detection may include generating post-amplification melting or annealing data to discriminate among *B. burgdorferi*, *B. afzelii*, and *B. garinii* by melting denaturation curve or melting temperature (Tm).

The present invention includes triplex assays as described above for all three pathogenic sequences and quadruplex assays that further include a human or can include other mammalian genetic target.

In another aspect, the invention features a method, which includes primer-dependent amplification, preferably PCR amplification, of three target sequences of three pathogens: Lyme spirochetes, *A. phagocytophilum* and *Babesia* species. Amplification reactions useful in methods of this invention may be any suitable exponential amplification method, including the polymerase chain reaction (PCR), either symmetric or non-symmetric, digital PCR, the ligase chain reaction (LCR), the nicking enzyme amplification reaction (NEAR), strand-displacement amplification (SDA), nucleic acid sequence-based amplification (NASBA), transcription-mediated amplification (TMA), and rolling circle amplification (RCA). Preferred methods utilize PCR. In nonsymmetric PCR amplification methods, for example asymmetric PCR, one primer, the primer synthesizing non-target strand, is present in a limiting amount so as to be exhausted prior to completion of amplification, after which linear amplification occurs using the remaining primer, the excess primer that synthesizes the probe binding target strand. A non-symmetric PCR method useful in this invention is LATE-PCR [see, for example, European Patent EP 1,468,114; and Pierce, et al. (2005) Proc Natl Acad Sci USA 102:8609-8614]. Preferred methods also include digital PCR [see, for example, Vogelstein and Kinzler (1999) Proc Natl Acad Sci USA 98:9236-9241].

The invention also provides PCR methods comprising contacting sample DNA with a pair of amplification primers for each target sequence, and performing repeated thermal cycles of primer annealing, primer extension, and strand denaturation (strand melting). Primer annealing may be performed at a temperature below the primer-extension temperature (for example, three-temperature PCR), or primer annealing and primer extension may be performed at the same temperature (for example, two-temperature PCR). The overall thermal profile of the reaction may include repetitions of a particular cycle, or temperatures/times may be varied during one or more cycles.

Assay methods according to this invention include detection of amplified target sequences using fluorescently or luminescently labeled hybridization probes that signal upon hybridization to target sequences, namely the amplification products of the PCR or other amplification reactions. Suitable probes include TaqMan probes and molecular beacon probes ("molecular beacons"), which are preferred. Detection may be performed during the course of amplification (real-time detection) or following amplification (end-point detection) using probes present in the starting amplification reaction mixture in a single tube, plate well, or other reaction vessel (homogeneous detection). Alternatively, detection may be performed in a melting or annealing step following amplification. Real-time detection, end-point detection and post-amplification thermal profiling are preferably performed in a homogeneous detection assay wherein probes are present in the starting amplification reaction mixture. Then again, using a microfluidic device, amplified products can be moved to a chamber in which they contact one or more detection probes as well, in some embodiments, or isolating reagents such as immobilized capture probes.

Primers and probes useful in methods, reaction mixtures and kits of this invention are oligonucleotides in the broad sense, by which is meant that they may be DNA, RNA, mixtures of DNA and RNA, and they may include non-natural nucleotides (for example, 2'-O-methyl ribonucleotides), non-natural internucleotide linkages (for example, phosphorothioate linkages), and DNA mimics (for example, PNA or LNA). Both primers and probes function in part by hybridizing to a sequence of interest in a reaction mixture. In the Examples below we utilize primers and probes that are DNA, which we prefer.

In another embodiment, the present invention further comprises a method of determining the appropriate treatment regimen by performing the above method and then administering the most effective treatment for that specific *Borrelia* species or other pathogens.

In a further embodiment, the present invention provides an automated multiplex diagnostic test for three or more species of Lyme disease.

It further provides a method of for accurate diagnosis of the disease(s) and then determining the appropriate treatment regimen for the specific causative pathogen(s), bacteria or eukaryotic parasite.

Another embodiment of the present invention provides an automated multiplex diagnostic test for simultaneous detection of all three prevalent species of Lyme disease spirochetes.

This invention includes reagent mixtures for performing methods according to this invention, as well as kits of reagents for preparing such reaction mixtures and for performing such methods. In one example, a kit for diagnosing a tick-borne disease comprises (i) a first pair of primers and a first molecular beacon probe for a first target selected from a group consisting of a recA gene sequence of *Borrelia* that differs among *B. burgdorferi, B. afzelii*, and *B. garinii*; a BmTPK gene sequence of *B. microti*; and an APH 1387 gene sequence of *A. phagocytophilum*, and (ii) a second pair of primers and a second molecular beacon probe for a second target selected from said group. The primer pairs define amplicons that are 70-300 base pairs in length, and each molecular beacon probe is labeled with a spectrally distinguishable fluorescent or luminescent signaling moiety, The kit can include a third pair of primers and a third molecular beacon probe for a human DNA gene sequence. In some embodiments, the first or second pair of primers can be selected from the group consisting of SEQ ID Nos. 10 and 11, SEQ ID Nos. 12 and 13, SEQ ID Nos. 14 and 15, SEQ ID Nos. 18 and 19, SEQ ID Nos. 24 and 25, and SEQ ID Nos. 26 and 27. The first or second molecular beacon probe can be selected from the group consisting of SEQ ID Nos. 5, 16, and 20. The human DNA gene can be the ACT A1 gene and in that case, the third pair of primers can have the sequences of SEQ ID Nos. 21 and 22, respectively, and the third molecular beacon probe can have the sequence of SEQ ID No. 23. The invention can also include slight modification of the normal molecular probes within the said amplicons specific for each *Borrelia* species tagged with different fluorophore to distinguish different species of these pathogens or can include the sloppy molecular beacons within the region for detection [see, for example, European Patent EP 1 921 169], such as the RecA3 probe described below.

Preferred reagent mixtures and kits according to this invention include buffers, salts, dNTPs, DNA polymerase, primers for the intended targets, and molecular beacon probes for the intended target sequences.

The details of one or more embodiments of the invention are set forth in the description below. Other features, objects and advantages of the invention will be apparent from the description and the claims.

Figure 1:
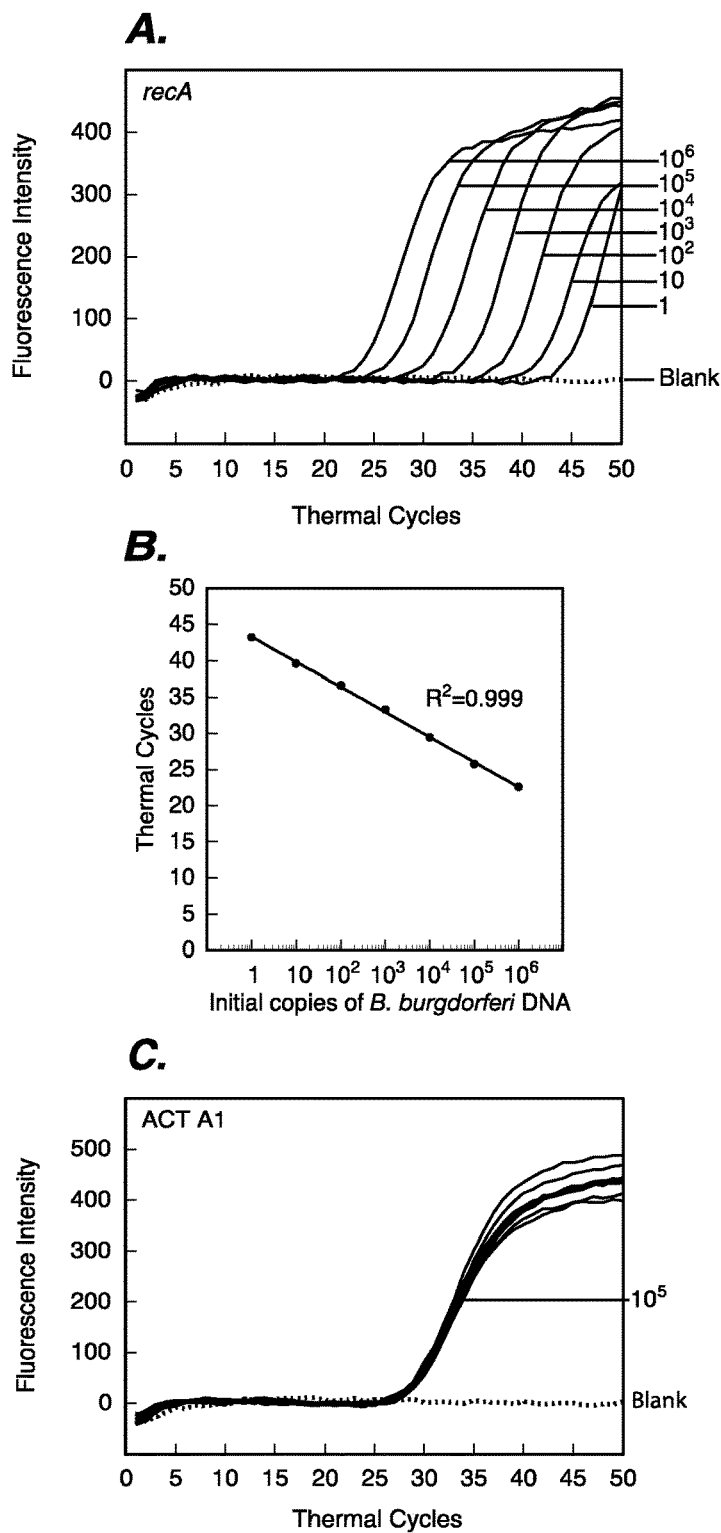
FIGS. 1A-C are a set of graphs showing (A) real-time fluorescence (fluorescence intensity versus cycle number)

for the RecA3 probe for different starting concentrations ($10^6$ to $10^0$) of *B. burgdorferi* target in the assay of Example 1; (B) PCR threshold cycle versus starting concentration of *B. burgdorferi* from FIG. 1A; and (C) real-time fluorescence for the ACTA1 probe in the assay of Example 1.

FIGS. 2A and B are a set of graphs showing (A) hybridization melting (fluorescence intensity versus temperature) of the RecA3 probe when the assay of Example 2 was performed with conserved oligonucleotides in all three *Borrelia* species: *B. burgdorferi, B. afzelii*, and *B. garinii*. and (B) melting curves (–dF/dT) of products of an asymmetric PCR using RecF3 and RecR3 primers and RecA3 molecular beacon with three *Borrelia* species, *B. burgdorferi, B. afzelii* and *B. garinii* genomic DNA as template.

Figure 3:
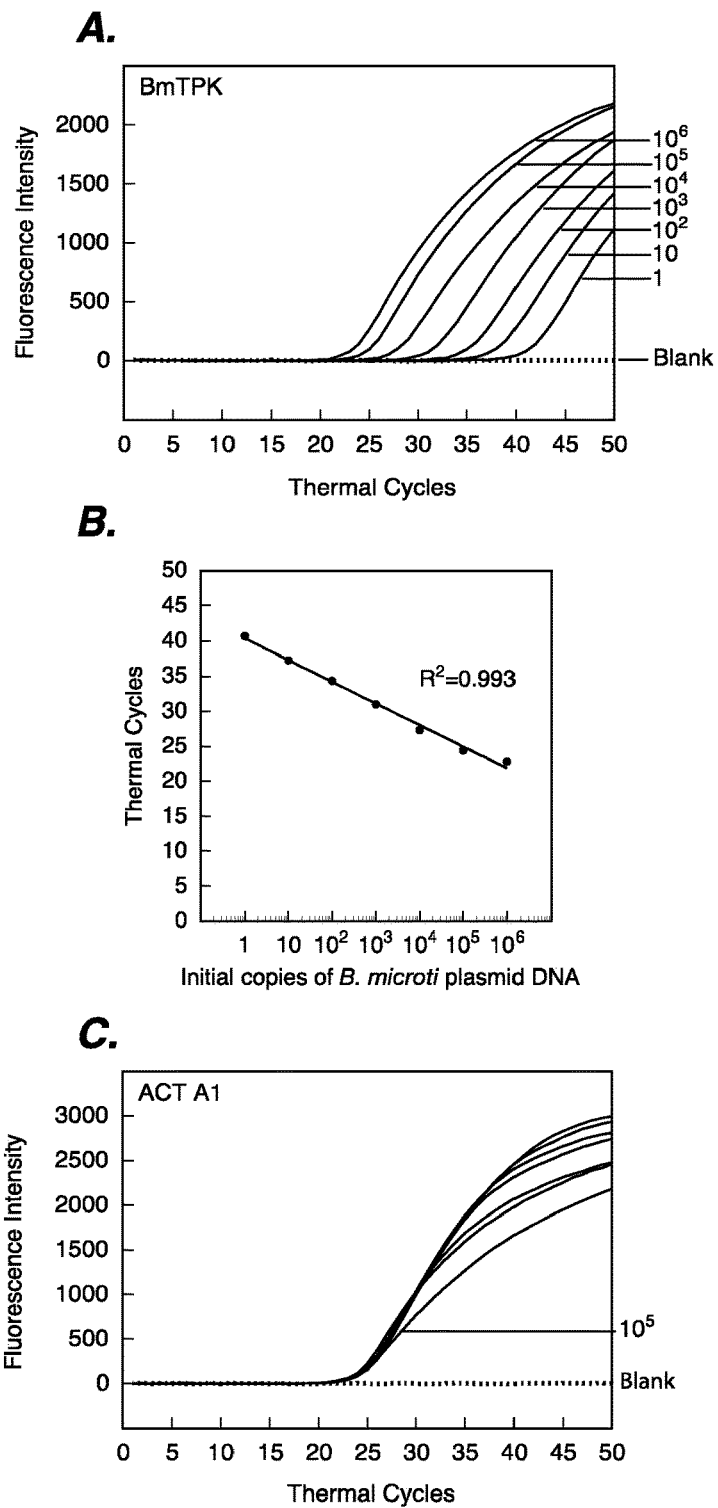

FIGS. 3A-C are a set of graphs showing (A) real-time fluorescence (fluorescence intensity versus PCR cycle number) for the BmTPK probe for different starting concentrations ($10^6$ to $10^0$) of *B. microti* target in the assay of Example 3; (B) PCR threshold cycle versus starting concentration of *B. microti* from FIG. 3A; and (C) real-time fluorescence for the ACTA1 probe in the assay of Example 3.

Figure 4:
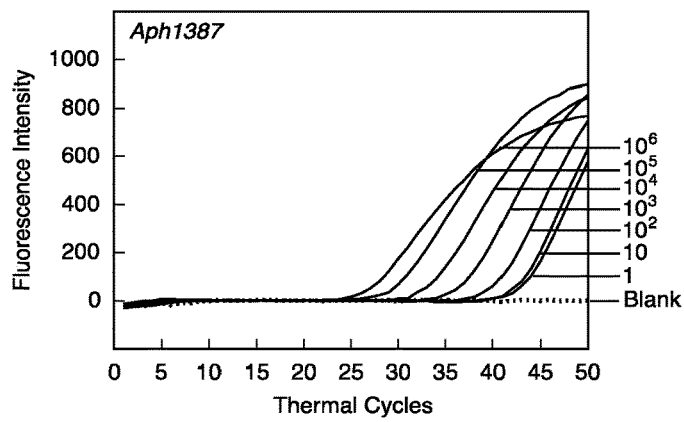
Figure 4:
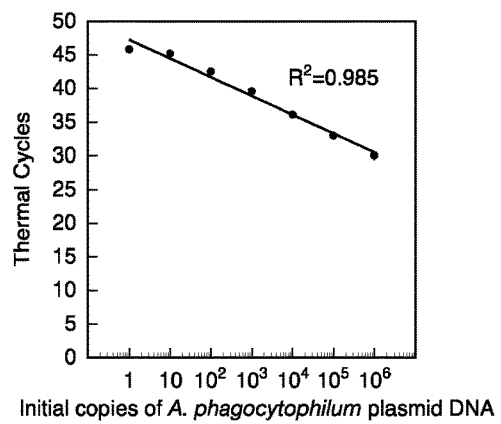
Figure 4:
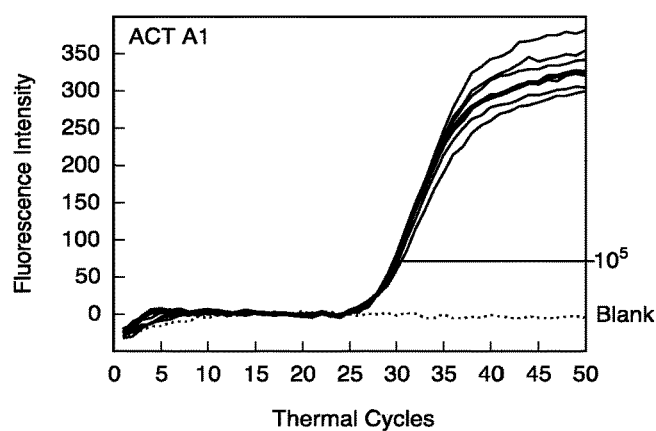

FIGS. 4A-C are a set of graphs showing (A) real-time fluorescence (fluorescence intensity versus PCR cycle number) for the Aph1387 probe for different starting concentrations ($10^6$ to $10^0$) of *A. phagocytophilum* target in the assay of Example 4; (B) PCR threshold cycle versus starting concentration of *A. phagocytophilum* from FIG. 4A; and (C) real-time fluorescence for the ACTA1 probe in the assay of Example 4.

FIGS. 5A-D are a set of graphs showing (A) of real-time fluorescence (fluorescence intensity versus PCR cycle number) for the RecA3 probe for different starting concentrations ($10^6$ to $10^0$) of *B. burgdorferi* target in the assay of Example 5; (B) real-time fluorescence (fluorescence intensity versus PCR cycle number) for the BmTPK probe for different starting concentrations ($10^6$ to $10^0$) of *B. microti* target in the assay of Example 5; (C) real-time fluorescence (fluorescence intensity versus PCR cycle number) for the Aph1387 probe for different starting concentrations ($10^6$ to $10^0$) of *A. phagocytophilum* target in the assay of Example 5; and (D) real-time fluorescence for the ACTA1 probe in the assay of Example 5.

Figure 6:
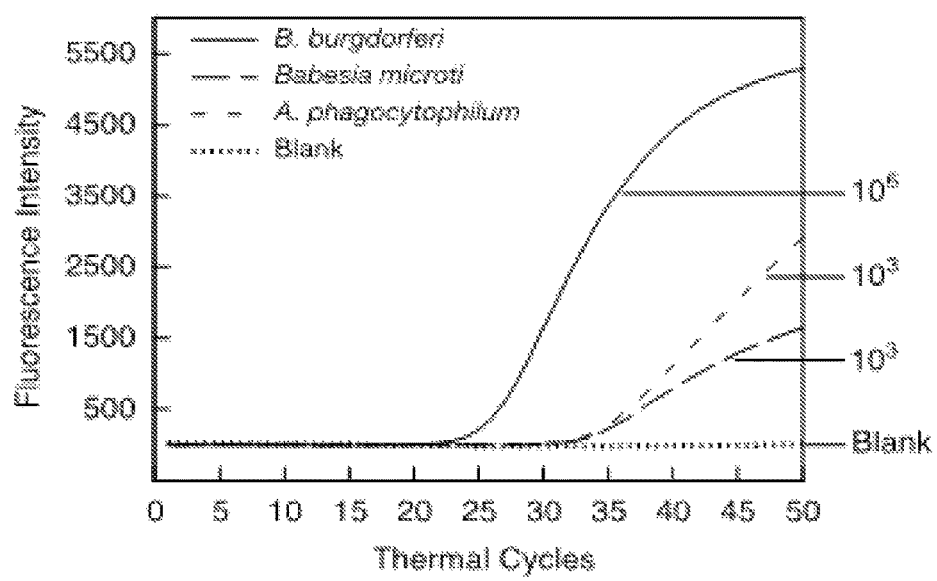

FIG. 6 is a graph of fluorescence intensity versus PCR cycle number for three probes in a triplex amplification starting with $10^6$ copies of *B. burgdorferi* genomic DNA (including $10^6$ copies of the recA gene) mixed with genomic copies of each of *A. phagocytophilum* and *B. microti* genomic DNA reflecting $10^3$ copies of the BmTPK and APH1387 genes in the assays of Example 6.

Figure 7:
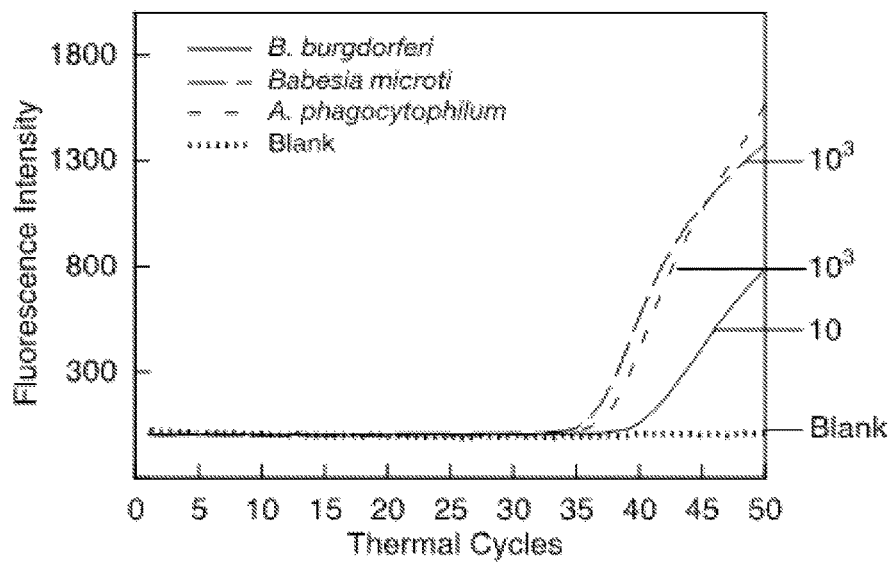

FIG. 7 is a graph of fluorescence intensity versus PCR cycle number for three probes in a triplex amplification starting with 10 copies of *B. burgdorferi* genomic DNA (including 10 copies of the recA gene) mixed with copies of each of *A. phagocytophilum* and *B. microti* genomic DNA reflecting $10^3$ copies of the BmTPK and APH1387 genes in the assays of Example 7.

DETAILED DESCRIPTION OF INVENTION AND EMBODIMENTS

The invention is based, at least in part, on unexpected discoveries that molecular beacon probes-based real-time polymerase chain reaction (PCR) can be used to diagnose Lyme disease, anaplasmosis and babesiosis in a sensitive and specific manner. Since microbial nucleic acids do not persist much longer after cure of a disease, PCR-based assays are ideal for detection of these three pathogens. As disclosed herein, the effective combinations of primers enable the amplification of target sequences specific to each infectious agent. In addition, the design of target-specific probes that are labeled with, e.g., differently colored fluorophores, in combination with the primers for each infectious agent allows one to unequivocally diagnose active disease caused by different tick-borne infections, individually or together. Before this invention, no one has yet been able to design and demonstrate the function of the desired multi-species combinations for testing blood samples from patients and for testing donated blood.

Due to the presence of nucleases in the serum, nucleic acids of the pathogens do not persist in the host much longer after the disease is cured [see Kurreck (2003), Eur J Biochem./FEBS 270:1628-1644; Meng et al. (2011) BMC Biotechnol 11:88; and Mutwiri et al. (2004) J. Control Release 97:1-17]. Therefore, PCR assays can be used as test of cure for various diseases. Selection of proper PCR target and conditions along with the use of efficient detection probe are critical for development of sensitive and specific diagnostic assays.

Molecular beacons are hairpin-shaped oligonucleotide probes that can be designed to be highly specific for their target sequences and can be labeled with distinguishably colored fluorophores [Marras et al. (2002) Nucleic Acids Res 30:e122]. The single-stranded loop of highly specific molecular beacons is designed to be complementary to a unique gene sequence that identifies the infectious agent. Drs. Marras, Tyagi, and Kramer used these probes to distinguish alleles that differ by as little as a single nucleotide polymorphism [Marras et al. (1999) Genet Anal 14:151-156; Piatek et al. (1998) Nat Biotechnol 16:359-63; Tyagi et al. (1998) Nat Biotechnol 16:49-53; and Tyagi et al. (2000) Nat Biotechnol 18:1191-1196]. The basis of this extraordinary specificity is that hairpin-shaped probes can assume two different stable states, by: (i) forming double-stranded hybrids with their target sequence, or (ii) retaining their partially double-stranded structure when not bound to a target. Any mismatch between the probe sequence of the molecular beacon and the target sequence destabilizes the probe-target hybrid, leading to return of the molecular beacon in its stable hairpin structure [Bonnet et al. (1999) Proc Natl Acad Sci USA 96:6171-6176; and Mhlanga and Malmberg (2001) Methods 25:463-471]. Thus, molecular beacon probes are inherently more specific than linear TaqMan probes, which are more stable when bound to their target, whether or not they are fully complementary to the target [Bonnet et al. (1999) Proc Natl Acad Sci USA 96:6171-6176; Petersen et al. (2004) Mol Cell Probes 18:117-122; and Tapp et al. (2000) Biotechniques 28:732-738]. The specificity of molecular beacon probes to detect the recA gene of *B. burgdorferi*, and to quantitate the number of spirochetes present in infected mouse tissue was previously reported [Saidac et al. (2009) BMC Microbiol 9:43-52].

The present invention involves assays that work in the presence of human DNA, such that they are useful as a diagnostic test for human Lyme disease. The methods for diagnosing active disease of the present invention detect three major Lyme spirochete species, *B. burgdorferi* sensu stricto, *B. afzelii*, and *B. garinii* in the same real time-PCR assay. An alternative aspect of the invention separate PCR assays are utilized by selecting the sequence-specific molecular beacon probes for each species. This present invention includes highly sensitive and multiplex real-time-PCR (rt-PCR) assay methods using target-specific molecular beacons that can distinguish *B. burgdorferi*, *A. phagocytophilum* and *B. microti* simultaneously in the same assay.

Certain embodiments of assays of this invention employ real-time PCR amplification with homogeneous detection of target DNA sequence of each of these three infectious-organism targets. The assays can be extended to include reverse transcription for detection of RNA, if needed. Previously, TaqMan probes developed by Applied Biosystems, which are single stranded oligonucleotides labeled with a fluorophore-quencher that hybridize with the sequence present in the internal region of an amplified PCR product have been used for detection of Lyme spirochetes in ticks and mammals. When free in solution, TaqMan probes form random coils in which fluorophore reporter and quencher come in close proximity, enabling Fluorescence Resonance Energy Transfer (FRET) from the fluorophore to the quencher. This mechanism alleviates the fluorescence signal of the reporter. In the presence of the target, TaqMan probe-target hybrid comes in contact with the Taq Polymerase during the extension phase of PCR cycles. Inherent 5'exonuclease activity of the enzyme then cleaves the probe, releasing the fluorescent reporter from the portion of the probe that includes the quencher. This leads to increase in the fluorescence intensity at each PCR cycle since FRET cannot occur anymore. Random coil formation of the free TaqMan probes sometimes results in only partial quenching of fluorescence in the absence of the specific target. Thus, TaqMan probes have not proven effective in diagnosing active disease caused by tick-borne pathogens.

This invention employs molecular beacons, which are dual fluorescently labeled single-stranded oligonucleotide probes that form stem-and-loop structures, such that the target-recognition sequence is located, entirely or predominantly, in the loop region and complementary terminal sequences (arms) form a stem bringing the fluorophore and quencher into close proximity [Marras et al. (1999) Genet Anal 14:151-156; Mazepa et al. (2010) J Am Anim Hosp Assoc 46:405-412; Tyagi et al. (2000) Nat Biotechnol 18:1191-1196; and Vannier et al. (2008) Infectious Disease Clinics of North America 22:469-488, viii-ix]. The quenching of fluorescence by contact is highly efficient and exhibits minimal background fluorescence in the absence of target sequences. The technology previously described for the use of molecular beacons as probes for PCR amplification products (amplicons) is significantly improved upon for this invention. Multiple molecular beacons can be labeled with different fluorophores, and several different probes can be used simultaneously in multiplex assays. Quenching of signal in the absence of the target is much more pronounced when molecular beacons are used as probes resulting in minimal background fluorescence when the probes are present in solution. In addition, molecular beacons can be designed to successfully discriminate single nucleotide polymorphisms (SNPs). Preferred assays according to this invention distinguish various Lyme spirochete species that show SNPs in the PCR-amplified region of the recA gene.

Previously, a 222-bp amplicon from recA gene of *B. burgdorferi* using RecF (forward) and RecR (reverse) primers was amplified in a real-time PCR assay using SYBR Green DNA dye for spirochete quantitation. In the present invention the same primers were used with a *Borrelia*-specific molecular beacon probe designated "RecA3", whose sequences are all given in Table 1 below. The recA sequence defined by the RecF and RecR primers is:

```
                                               (SEQ ID No. 1)
5'GTGGATCTATTGTATTAGATGAGGCTCTCGGCATTGGCGGATATCCT

AGGGGGCGCATAATAGAAATTTTTGGCCCCGAGTCGTCTGGCAAGACTA

CTTTAACTCTTCAAGCGATTGCTGAGGTGCAAAAAGAAGGTGGGATAGC

TGCTTTTATTGATGCTGAGCATGCTCTTGATCCTGTTTATGCAAAAGCT

TTAGGTGTTAATGTTGCAGAACTTTGGC3'
```

Three sequences are underlined: the sequence of the RecF primer, the sequence complementary to the RecR primer (SEQ ID No. 17), and the sequence of the molecular beacon RecA3 probe's target-recognition sequence (which in this case is the loop sequence plus multiple nucleotides of each arm) (bold-underlined). Presented below is the sequence of the complementary strand of *B. burgdorferi* in the region to which the RecA3 probe binds, plus the corresponding sequences of *B. afzelii* and *B. garinii* that are complementary to the loop plus additional stem-nucleotides of the RecA3 probe, which is shown in 3'→5' direction for visualizing hybridization and mismatch.

```
    B. burgdorferi
                                      (SEQ ID No. 2)
    5' TTAT GCGCCCCCTAGGATATCCGCCA ATGC 3'

B. afzelii
                                      (SEQ ID No. 3)
    5' TTAT GCGCCCCCTAGGATATCCACCA ATGC 3'

B. garinii
                                      (SEQ ID No. 4)
    5' TTAT TCGCCCCCTAGGATATCCACCA ATGC 3'

RecA3 probe
                                      (SEQ ID No. 5)
    3' GAC CGCGGGGGATCCTATAGGCG GTC 5'
```

In the above sequences, spaces have been left before and after the regions of complementarity for illustrative purposes. As indicated, the molecular beacon probe (SEQ ID No. 5) includes a probe sequence consisting of the loop (SEQ ID No. 30) and three nucleotides of each arm (bold) that is perfectly complementary to the *B. burgdorferi* sequence (SEQ ID No. 2). The probe is complementary to, but not perfectly complementary to, the other species, particularly the target sequences of *B. afzelii* (SEQ ID No. 3) and *B. garinii* (SEQ ID No. 4), which possess one (*B. afzelii*) or two (*B. garinii*) single nucleotide polymorphisms (SNPs) facilitating differentiation of species by post-PCT Tm determination. Target nucleotides that are mismatched from the probe sequence are bolded and underlined. Probe nucleotides forming the stem are underlined.

As indicated above, the RecF and RecR primers define a 222 base-pair (bp) amplicon that includes the sequence probed by the RecA3 probe. As will be appreciated, other primers could be chosen to produce an amplicon including that sequence, as by sliding the current primers along the sequence of the recA gene. Primer design is well known and takes into account the amplification mixture and protocol intended to be used. Similarly, the loop sequence of a probe intended to be perfectly complementary to the *B. burgdorferi* species in the region of interest could be varied by sliding the loop along the sequence of the gene sequence or by changing its length. Once again the amplification parameters intended to be used are taken into account. The "Beacon Designer™" computer program often suggests multiple loop sequences to choose from.

The RecA3 molecular beacons probe is labeled with a fluorescent moiety on one end (in the embodiment used in the Examples a Fluorescein (FAM) reporter molecule at the 5' terminus) and a non-fluorescent quencher moiety on the other end (in the embodiment used in the Examples a Black Hole Quencher 1 (BHQ-1) at the 3' terminus). As will be appreciated, other fluorescent or luminescent moieties could be used as labels, as could different non-fluorescent quencher moieties. Molecular beacon RecA3 has been shown to be highly efficient and sensitive for the detection and quantification of *B. burgdorferi* in the infected mammalian (mouse) tissues by real-time PCR. Preferred assays according to this invention include also amplifying a human target DNA sequence as a positive control to employ with the human samples. In the Examples, we utilize for this purpose primers and a probe for a target sequence in the single-copy Act A1 gene. In the embodiment utilized in the Examples the molecular beacon probe, designated ACTA1, is labeled on one end with a fluorescent moiety and on the other end with a non-fluorescent quencher moiety (in the Examples a Quasar 670 fluorophore and Black Hole Quencher 2 (BHQ-2) quencher. This human PCR target and probe provide a positive control to determine the quality of DNA isolated from human patient samples.

The 325 bp ACT A1 amplicon is derived from exon 3 (Accession No. NG006672) and the 104 nucleotide sequence obtained by using 5ACTA1 and 3ACTA1 primers is:

(SEQ ID No. 6)
5'AGAGCAAGAGAGGTATCCTGACCCTGAAGTACCCTATCGAGCACGGC

ATCATCACCAACTGGGATGACATGGAGAAGATCTGGCACCACACCTTCT

ACAACGAG3'

Three sequences are underlined: the sequence the 5ACTA1 primer, the sequence complementary to the 3ACTA1 primer, and the sequence of the ACTA1 molecular beacon's (SEQ ID No. 23) probe sequence, which in this case is the loop sequence (bold-underlined, SEQ ID No. 28).

The Act A1 gene-segment target can be used in multiplex assays to detect *B. burgdorferi* DNA in the presence of human DNA. Indeed, sensitivity of detection of *B. burgdorferi* remained unaffected in the multiplex assays relative to that in the monoplex assay when *B. burgdorferi* DNA alone is present.

The primers for the *B. microti* TPK gene, the *A. phagocytophilum* APH 1387 gene, and the human ACT A1 gene were chosen to target regions that distinguish the respective organisms but are believed to be quite conserved regions among species and strains of the respective targets. Amplification conditions were taken into account, as all primer pairs were intended to amplify efficiently in a single multiplex assay. Molecular beacon probes for these targets can be designed using the Beacon Designer™ computer program, so that they too would work in a single multiplex assay.

Certain assays according to this invention amplify and detect a *Borrelia* target sequence that differs among *B. burgdorferi*, *B. afzelii*, and *B. garinii*. Embodiments of such assays can utilize three differently colored *Borrelia* molecular beacon probes: one allele-discriminating probe that is perfectly complementary to each species [see, Tyagi et al. (1998) Multicolor molecular beacons for allele discrimination. Nat Biotechnol 16:49 53]. Preferred embodiments utilize a single mismatch-tolerant probe that hybridizes to all three species with a detectably distinct melting temperature (Tm) for each species. In one preferred embodiment the probe's target-complementary sequence is perfectly complementary to one species (particularly for assays intended for use in the USA., that species is *B. burgdorferi* sensu stricto, whereas for assays intended for use in Europe, those species are *B. burgdorferi*, *B. afzelii*, and *B. garinii*). Assays utilizing a single *Borrelia* probe are simpler to manufacture, and they utilize less color space of an instrument. As shown in Example 2 below, using the RecA3 probe, melting curves were able to distinguish among three species. A post-amplification melting or annealing curve can potentially be used to identify which species is present in a sample, if the Tm's are at least 3° C., preferably at least 5° C., apart. In one embodiment a different set of primers that are perfectly conserved in all three *Borrelia* species was used to obtain a slightly longer, 287 bp size amplicon and the same, RecA3 molecular beacon in the assay. The target sequence for the *B. burgdorferi* is given below:

(SEQ ID No. 7)
5'<u>GCAAGAGTTCAAATAGAAAAA</u>GCTTTTGGAAAGGGAAGTCTTATTA

AGATGGGGGAATCTCCTGTTGGACAAGGTATAAAAAGTATGTCAAGTG

GATCTATTGTATTAGATGAGGCTCTCGGCATTGGCGGATATCCTAGGG

GGCGCATAATAGAAATTTTTGGCCCCGAGTCGTCTGGCAAGACTACTT

TAACTCTTCAAGCGATTGCTGAGGTGCAAAAAGAAGGTGGGATAGCTG

CTTTTATTGATGCTGAGCATGCTCTTGATC<u>CTGTTTATGCAAAAGCTT</u>

<u>T</u>3'

Two sequences are underlined: the RecF3 primer and the sequence complementary to RecR3 primer. Nucleotides depicting the RecA3 probe are marked by bold letters.

Embodiments of assays according to this invention are multiplex assays that include detection of *B. microti* and *A. phagocytophilum* in addition to *Borrelia*. For the parasite *B. microti* (and other *Babesia* species) we disclose a preferred embodiment of PCR primers 5BmTPK and 3BmTPK for amplifying a 141-base-pair (bp) sequence of the BmTPK gene (Accession No. FO082871), using the primers and a molecular beacon probe specific for that sequence, which is as follows:

(SEQ ID No. 8)
5'TGAGAGGAACGACCATAGCCTTTTACATATGACACAAGCTATAACT

ATAGCAGAAAATGGAATTTCGGTGTTGTTGACCAGCGGCCGCGAAGAA

GGATGGCCAATTTTTCCAAGACATTTTTCGTGTGATTTACCTGATGG3'

Three sequences are underlined: the 5BmTPK primer, the sequence complementary to the 3BmTPK1 primer, and the BmTPK probe's loop sequence (bold-underlined). Note that two additional probe nucleotides, TC located 5' to the loop sequence, are complementary to the target sequence.

For *A. phagocytophilum* we disclose a preferred embodiment of PCR primers for amplifying a 152 bp sequence of the APH1387 gene (Accession No. CP000235), obtained by using 5Aphagocyt and 3Aphagocyt primers and APH1387 molecular beacon probe specific for that sequence. The sequence of the amplicon is:

```
                                                        (SEQ ID No. 9)
5'ATGGCTACTACGAAGGATGTGCTTGTGACAAAGATGCCAGCACTAAT

GCGTACTCGTATGACAAGTGTAGGGTAGTACGGGGAACGTGGAGACCGA

GCGAACTGGTTTTATATGTTGGTGATGAGCATGTGGCATGTAGAGATGT

TGCTTCG3'
```

Three sequences are underlined: the 5Aphagocyt primer, the sequence complementary to the 3Aphagocyt primer, and the APH1387 probe's loop sequence (bold-underlined, SEQ ID No. 29).

Both of the foregoing primer pairs and the probe are adapted to work with the *Borrelia* primers and probe in a real-time or end-point multiplex PCR assay. The present invention demonstrates that a multiplex PCR assay for all three targets can also include primers and a probe for human DNA. Furthermore, our single quadruplex assay is able to distinguish all three major *Borrelia* species implicated in Lyme disease in humans. Additionally, by including primers and a probe for human DNA, assays according to this invention are quantitative for the starting levels of the pathogenic targets.

The present invention provides a novel multiplex assay method to diagnose three tick-borne illnesses. It comprises a sensitive, specific and user-friendly method of diagnosing Lyme disease, as well as tick-borne pathogens comprising *A. phagocytophilum* and *Babesia* species by obtaining a biological sample from a human or other mammal and detecting the DNA of one or more of the three major Lyme spirochetes and at least one of *A. phagocytophilum* and *Babesia* species, preferably both. Preferred embodiments also include detecting human DNA as a positive control that determines quality of DNA and permits quantitation of results. Our most preferred assay is a quadruplex PCR assay that utilizes a single *Borrelia* probe having distinguishable Tm's against the three *Borrelia* species. Alternatively, once a determination is made regarding presence of *Borrelia* in the sample in the amplification part of the multiplex assay, a follow up assay can be performed to identify the specific *Borrelia* species using a complement of primers, for example, species-specific primers, and molecular beacon probes, for example, species-specific probes, whose colors or color identify which species is present. A further alternative, utilizing species-specific *Borrelia* probes as stated above, would include five molecular beacon probes, or six, if a human DNA target such as the Act A1 gene is included. The above method further provides a basis of determining the appropriate treatment and then employing the most effective treatment regimen for that specific pathogen, especially during the late persistent disease.

The present invention resolves a serious unmet need in the diagnosis and prognosis of Lyme disease, anaplasmosis and babesiosis. Current serology based tests for these diseases cannot distinguish whether the patient formerly had the disease or is still infected. Furthermore, reinfection cannot be detected using the serological tests, which is of particular importance in the endemic regions. The present invention will be able to diagnose the active disease phase and will be able to classify the infection based upon the particular tick-borne pathogen.

Nucleic acid-based diagnostic tests for infectious diseases are becoming increasingly useful. Applicants previously developed and assessed a real-time PCR based test that incorporated specific molecular beacon probes against the recA gene of Lyme disease-causing *Borrelia burgdorferi* to detect and quantify this spirochete in infected mouse tissues [Saidac et al. (2009) BMC Microbiol 9:43-52]. The present invention converts the test for patients and provides a sensitive, specific and accurate test for diagnosis of Lyme disease in the endemic regions of both the United States and Europe and certain regions of Asia where the disease is prevalent. This assay can detect two additional tick-borne emerging pathogenic agents responsible for devastating and often fatal diseases, anaplasmosis and babesiosis, along with Lyme disease-causing *Borrelia* species simultaneously.

The present invention represents several advantages over the current science, specifically with the use of real time-PCR (rt-PCR) and specific probes. This method offers a decrease in turn-around time, increased reliability and efficiency, and greater accuracy. In addition, automation of nucleic acid extraction coupled with rt-PCR results in a fast and accurate platform for diagnosis and a closed system prevents cross-contamination. Finally, internal positive and negative controls (sample without template) can ensure good quality of the prepared samples, confirm the sensitivity and accuracy of the test, and ensure lack of contamination. Importantly, this aspect of the present invention provides a method of selecting an appropriate treatment and determining the efficacy of the administered therapy in a timely manner.

The assay of the present invention can be optimized to detect the presence of the DNA for a sensitive and specific diagnosis of the active Lyme disease. Therefore, it is expected that the subjects, especially those exhibiting persistent manifestations will directly benefit from the study. Furthermore, use of the sequence specific molecular beacon probes designed for the selected specific real-time polymerase chain reaction amplicon for each tick-borne pathogen and labeled with different fluorophores will lead to the development of a very sensitive, specific and confirmatory diagnostic assay for single or multiple tick-borne co-infecting pathogens. Already standardized recA amplicons and specific molecular beacons can potentially be used to distinguish three species of Lyme spirochetes in this assay. In addition, a PCR amplicon of APH1387 gene, which encodes a unique *A. phagocytophilum* protein essential for its pathogenesis and unique region of the TPK-encoding gene of *Babesia* species and respective sequence specific molecular beacons designed and optimized for these amplicons can be included in the multiplex assay. Hence, a single test will be able to identify the presence of one or more tick-borne pathogens in the patients. Although molecular beacon probes have been used for diagnosis of some diseases, such as tuberculosis, such a test for Lyme disease and other tick-borne emerging pathogens does not exist. This test will not only be more sensitive and specific for the active disease, it will ultimately diagnose multiple tick-borne diseases simultaneously.

In one embodiment, the present invention comprises a sensitive, specific and user-friendly method of diagnosing Lyme disease, even detecting the DNA of one or more of the three major Lyme spirochetes as well as tick-borne pathogens comprising *A. phagocytophilum* and *Babesia* from the same biological sample from a mammal. It provides the distinct advantage over the current methods, as it comprises a single test and can diagnose multiple tick-borne diseases simultaneously within a few hours. In addition, the assay will detect both bacterial and parasitic pathogens commonly present (*B. burgdorferi* that causes Lyme disease) or emerging *A. phagocytophilum* that causes Human Granulocytic Anaplasmosis, i.e., HGA, and *Babesia* species that causes babesiosis, respectively.

In another embodiment, the present invention further comprises a method of determining the appropriate treatment regimen by performing the above method and then administering the most effective treatment for that specific spirochete. Since treatment strategies are different for bacterial and parasitic pathogens, a simultaneous and accurate detection of the pathogen will help design better treatment regimes for the co-infections with the emerging tick-borne pathogens, especially for the patients in the endemic regions of the United States and Europe.

In a further embodiment, the present invention provides an automated multiplex diagnostic test for three or more species of Lyme disease.

It further provides a method of for accurate diagnosis of the disease(s) and then determining the appropriate treatment regimen for the specific causative pathogen(s), bacteria or eukaryotic parasite.

Another embodiment of the present invention provides an automated multiplex diagnostic test for simultaneous detection of all three prevalent species of Lyme disease spirochetes and their differentiation.

Another embodiment of the present invention is selection of the specific segments of genes of *A. phagocytophilum* and *Babesia microti*, two emerging tick-borne pathogens, Aph1387 and thiamine pyrophosphokinase (TPK) respectively and design of the primers and molecular beacon probes for their amplification and detection at the conditions that are used for amplification of recA and ACT A1 amplicons of *B. burgdorferi* and humans, respectively. Molecular beacon probes for Aph1387 amplification product are labeled with fluorophore CAL Fluor Red 610 with BHQ-2 as quencher and for TPK is labeled with CAL Fluor Orange 560 with BHQ-1 quencher. Both of these gene segments and fluorophores in molecular beacons are compatible for each other and a single multiplex PCR can detect the presence of DNA of each pathogen.

Another aspect of this invention is that an accurate and sensitive test for *Babesia* species will allow testing of blood in the blood banks to avoid transmission of this fatal disease through blood transfusion. As documentation of the cases of blood transfusion-associated babesiosis and resulting deaths have started appearing in the last few years, there is urgency to detect the parasite in the donated blood to prevent such transmission. Our assay conducted with the original blood samples or following blood culture in vitro provides an easy and cost-effective mechanism to achieve this objective.

One of the most important features of this invention is that design of the primers and molecular beacon probes and selection of the fluorophores for molecular beacons that are compatible with each other and do not exhibit noticeable interference. Furthermore, the optimized PCR conditions are such that amplification of gene segments, probe hybridization and detection of all four amplicons is possible in the same reaction. There is almost no competition in the PCR and probe hybridization as demonstrated by the sensitivity and specificity of detection of each target DNA according to their quantity present in both monoplex and multiplex assays. Thus, we have discovered that a single multiplex assay can both detect the presence of each target DNA and can also accurately quantify it. Although infections with bacterial pathogens, *B. burgdorferi* and *A. phagocytophilum*, can be treated with the same antibiotics, treatment of parasitic disease babesiosis requires different drug regime. Since the subjective symptoms for these tick-borne illnesses may overlap, a single assay that can discriminate the presence of one or more of these pathogens from this invention will allow appropriate treatment of the patients in a timely manner.

A "nucleic acid" refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA.

As used herein, the term "target nucleic acid" or "target sequence" refers to a nucleic acid containing a target nucleic acid sequence. A target nucleic acid may be single-stranded or double-stranded, and often is DNA, RNA, a derivative of DNA or RNA, or a combination thereof. A "target nucleic acid sequence," "target sequence" or "target region" means a specific sequence comprising all or part of the sequence of a single-stranded nucleic acid. A target sequence may be within a nucleic acid template, which may be any form of single-stranded or double-stranded nucleic acid.

As used herein the term "amplification" and its variants includes any process for producing multiple copies or complements of at least some portion of a polynucleotide, said polynucleotide typically being referred to as a "template." The template polynucleotide can be single stranded or double stranded. A template may be a purified or isolated nucleic acid, or may be non-purified or non-isolated. Amplification of a given template can result in the generation of a population of polynucleotide amplification products, collectively referred to as an "amplicon." The polynucleotides of the amplicon can be single stranded or double stranded, or a mixture of both. Typically, the template will include a target sequence, and the resulting amplicon will include polynucleotides having a sequence that is either substantially identical or substantially complementary to the target sequence. In some embodiments, the polynucleotides of a particular amplicon are substantially identical, or substantially complementary, to each other; alternatively, in some embodiments the polynucleotides within a given amplicon can have nucleotide sequences that vary from each other. Amplification can proceed in linear or exponential fashion, and can involve repeated and consecutive replications of a given template to form two or more amplification products. Some typical amplification reactions involve successive and repeated cycles of template-based nucleic acid synthesis, resulting in the formation of a plurality of daughter polynucleotides containing at least some portion of the nucleotide sequence of the template and sharing at least some degree of nucleotide sequence identity (or complementarity) with the template. In some embodiments, each instance of nucleic acid synthesis, which can be referred to as a "cycle" of amplification, includes creating free 3' end (e.g., by nicking one strand of a dsDNA) thereby generating a primer and primer extension steps; optionally, an additional denaturation step can also be included wherein the template is partially or completely denatured. In some embodiments, one round of amplification includes a given number of repetitions of a single cycle of amplification. For example, a round of amplification can include 5, 10, 15, 20, 25, 30, 35, 40, 50, or more repetitions of a particular cycle. In one exemplary embodiment, amplification includes any reaction wherein a particular polynucleotide template is subjected to two consecutive cycles of nucleic acid synthesis. The synthesis can include template-dependent nucleic acid synthesis.

The term "primer" or "primer oligonucleotide" refers to a strand of nucleic acid or an oligonucleotide capable of hybridizing to a template nucleic acid and acting as the initiation point for incorporating extension nucleotides according to the composition of the template nucleic acid for nucleic acid synthesis. "Extension nucleotides" refer to any nucleotides (e.g., dNTP) capable of being incorporated into an extension product during amplification, i.e., DNA, RNA, or a derivative if DNA or RNA, which may include a label.

The term "probe" as used herein refers to an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled with a label such as fluorophore or biotin to which a streptavidin complex may later bind.

Complement" or "complementary" as used herein to refer to a nucleic acid may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

"Hybridization" or "hybridize" or "anneal" refers to the ability of completely or partially complementary nucleic acid strands to come together under specified hybridization conditions (e.g., stringent hybridization conditions) in a parallel or preferably antiparallel orientation to form a stable double-stranded structure or region (sometimes called a "hybrid") in which the two constituent strands are joined by hydrogen bonds. Although hydrogen bonds typically form between adenine and thymine or uracil (A and T or U) or cytosine and guanine (C and G), other base pairs may form [e.g., Adams et al. (1992) The Biochemistry of the Nucleic Acids, 11th ed.].

As used herein, the term "contacting" and its variants, when used in reference to any set of components, includes any process whereby the components to be contacted are mixed into same mixture (for example, are added into the same compartment or solution), and does not necessarily require actual physical contact between the recited components. The recited components can be contacted in any order or any combination (or subcombination), and can include situations where one or some of the recited components are subsequently removed from the mixture, optionally prior to addition of other recited components. For example, "contacting A with B and C" includes any and all of the following situations: (i) A is mixed with C, then B is added to the mixture; (ii) A and B are mixed into a mixture; B is removed from the mixture, and then C is added to the mixture; and (iii) A is added to a mixture of B and C. For example, "contacting a template with a reaction mixture" includes any or all of the following situations: (i) the template is contacted with a first component of the reaction mixture to create a mixture; then other components of the reaction mixture are added in any order or combination to the mixture; and (ii) the reaction mixture is fully formed prior to mixture with the template.

EXAMPLES

The present invention is described more fully by way of the following non-limiting experimental examples. Modifications of these examples will be apparent to those skilled in the art and are intended to be within the scope of the invention, as described.

Materials and Methods

Microbial strains and human cell line. For standardization of conditions for the diagnostic assay for Lyme disease, N40 strain clone D10/E9, of *B. burgdorferi* (sensu stricto), VS461 strain of *B. afzelii* and PBi strain of *B. garinii* were grown in BSKII medium supplemented with 6% rabbit serum at 33° C. (E. Vannier of Tufts Medical Center at Boston, and E. Fikrig of Yale University School of Medicine provided the genomic DNA from *B. microti* strain RM/NS and *A. phagocytophilum* strain HZ, respectively.) Human embryonic kidney 293 cells were cultured in a 1:1 mix of DMEM (low glucose) and Ham's F12 medium (Invitrogen, CA) supplemented with 10% FBS to isolate DNA for the assays.

Isolation of *B. burgdorferi* and human genomic DNA. Total genomic DNA was isolated from the Lyme spirochetes grown to a density of $\sim 10^8$ spirochetes/ml using the protocol we described previously [Parveen and Leong (2000) Mol Microbiol 35:1220-1234]. DNA from 293 cells was isolated using the previously described protocol [Morrison et al. (1999) J Clin Microbiol 37:987-992) with two modifications. First, PLG-containing tubes (Qiagen Sciences, MD) were used for phenol and chloroform extraction, since they allow clean separation of the top aqueous layer by decantation after centrifugation. Second, a final step of passing the DNA through DNeasy kit columns (Qiagen Sciences) was included to obtain good quality DNA for rt-PCR.

Molecular beacons design. Design of molecular beacon probe to hybridize to the recA gene of Lyme spirochetes and tagged with FAM fluorophore and BHQ-1 quencher were described previously [Saidac et al. (2009) BMC Microbiol 9:43-52]. Other molecular beacon probes were designed using the previously described strategies such that fluorophore emission profiles are non-overlapping [Vet and Marras (2005) Methods Mol Biol 288:273-290]. Briefly, molecular beacon probes for; ACTA1 gene amplicon was tagged with Quasar 670 fluorophore and BHQ-2 quencher, BmTPK amplicon with CAL Fluor Orange 560 fluorophore and BHQ-1 quencher and APH1387 amplicon using CAL Fluor Red 610 and BHQ-2 quencher. The lengths of the probe sequences were chosen so that they would form a stable hybrid with the target at 5 to 10° C. above the annealing temperature (60° C.). of the PCR assay. The 5' and 3' arm sequences of the molecular beacons were designed to form a stable hybrid at 5 to 10° C. above the annealing temperature of the PCR assay. The fluorophores and quenchers were chosen based on the specifications of the spectrofluorometric thermal cycler platform on which the assays were carried out and their compatibility in one multiplex assay. The sequences of the molecular beacons used in this study are listed in Table 1. A detailed protocol for the synthesis and purification of molecular beacons can be found at molecular-beacons.org. For this study, molecular beacons were ordered from Biosearch Technologies, CA. Initial standardization of PCR conditions was conducted by using SYBR Green I dye (Life Technologies, CA) and was followed by replacing SYBR Green with specific molecular beacon probes in the assays.

Real-time PCR. Since genome sizes of *B. burgdorferi* and human are 1.5 Mb and 3.2 Gb respectively, 2 ng of *B. burgdorferi* genomic DNA contains approximately $10^6$ copies of recA gene, while 350 ng of human genomic DNA contains approximately $10^5$ copies of ACTA1 gene. Similarly, genome sizes of *B. microti* and *A. phagocytophilum* are 6.5 Mb and 1.47 Mb, respectively. Therefore, $10^6$ copies of thiamine pyrophosphokinase gene of *B. microti* (BmTPK) and APH1387 are calculated to be present in 8 ng and 2 ng, respectively. All primer and probe sequences are listed in Table 1. A 222 bp fragment from recA gene of *B. burgdorferi* using RecF and RecR primers and a 104 bp fragment from human alpha actin A1 (ACTA1) gene using 5ACTA1 and 3ACTA1 primers were amplified by PCR in 0.2 ml optical tubes using a Bio-Rad CFX96 Touch Real-time PCR system (Bio-Rad Life-Science Research, CA). Amplification was performed in 25 µl reaction mixtures containing Amplitaq Gold PCR reaction buffer (Life Technologies) supplemented with 3 mM MgCl2, 500 ng/µl of bovine serum albumin, 250 µM of each deoxynucleoside triphosphate (dNTP), 0.5 µM of each set of primers and 5U of Amplitaq Gold polymerase. For each amplification reaction, 5 µl of the sample was used to minimize the variation due to pipetting error. BmTPK gene of *B. microti* and APH1387 gene of *A. phagocytophilum* were amplified using the primers and cloned in TopoXL vector from Invitrogen to optimize conditions such that these two pathogens can be detected under the same conditions as Lyme spirochetes. Amplification of a 141 bp amplicon from BmTPK gene using 5BmTPK and 3BmTPK primers and a 152 bp amplicon of APH1387 gene using 5Aphagocyt and 3Aphagocyt primers were carried out. Molecular beacon probes, BmTPK and APH1387 were used for detection of the BmTPK and APH1387 amplicons, respectively. Data were processed using the software provided by the manufacturer.

For quadruplex real-time PCR assays, genomic DNA of *B. burgdorferi* and human, and clones of BmTPK and APH1387 were used as templates, and 500 nM each of RecF and RecR primers and 5BmTPK and 3BmTPK primers, 250 nM each of 5Aphagocyt and 3Aphagocyt primers, 100 nM each of 5ACTA1 and 3ACTA1 primers, 25 ng each of RecA3, BmTPK, APH1387, and ACTA1 molecular beacons were included in each reaction. The amplification program consisted of initial heating at 95° C. for 5 minutes, followed by 60 cycles of heating at 95° C. for 15 s, annealing and fluorescence detection at 60° C. for 30 s, and polymerization at 72° C. for 20 s. All assays were performed with a Bio-Rad CFX96 Touch Real-time PCR Detection System.

For confirmation of the quadruplex assay in which plasmids containing BmTPK and APH1387 were used, we incorporated different concentrations of genomic DNA of *B. burgdorferi*, *B. microti* (6.5 Mb) and *A. phagocytophilum* (1.47 Mb) in the triplex real time-PCR. Human DNA control was not included in these assays. By using different relative genomic copy numbers using the conditions similar to those described above for quadruplex assay, these confirmatory assays (FIGS. 6 and 7) validated our assay for simultaneous detection of all three pathogens.

To differentiate three major species that cause Lyme disease in Europe, *B. burgdorferi*, *B. afzelii* and *B. garinii*, asymmetric PCR assay was performed in 25 µl volume such that primer synthesizing the target strand of molecular beacon was used in excess. The primers for recA gene that are from the conserved region in all three species, RecF3 and RecR3 were designed to amplify a slightly longer, 287 bp fragment in this asymmetric PCR assay. The reaction mixture contained 1× Amplitaq Gold PCR buffer supplemented with 3 mM of MgCl2, 500 ng/µl of bovine serum albumin, 250 µM of each dNTP, 30 nM of RecF3 primer, 1000 nM of RecR3 primer, 12.5 ng of RecA3 molecular beacon and 5 units of Amplitaq Gold polymerase. The amplification program consisted of initial heating at 95° C. for 5 minutes, followed by 60 cycles of heating at 95° C. for 15 s, annealing and fluorescence detection at 60° C. for 30 s, and polymerization at 72° C. for 20 s. It was immediately followed by incubation at 25° C. for 2 minutes to allow annealing, and then a melt curve was included by increasing temperature from 25° C. to 95° C. in 1° C. step, with each step lasting 2 minutes while monitoring the fluorescence. For analysis, the first derivative of the denaturation profile was determined as described previously [El-Hajj et al. (2009) J Clin Microbiol 47:1190-1198].

TABLE 1

Sequence of PCR primers and molecular beacon probes

| PCR primers/ Probes | Sequence | Length | Tm (C) | Size of PCR amplicon | SEQ ID No. | Fluorophore/ Quencher |
|---|---|---|---|---|---|---|
| RecF | 5' GTG GAT CTA TTG TAT TAG ATG AGG CTC TCG 3' | 30 | 66.1 | 222 bp | 10 | |
| RecR | 5' GCC AAA GTT CTG CAA CAT TAA CAC CTA AAG 3' | 30 | 67.3 | | 11 | |
| RecA3 | 5' CTG GCG GAT ATC CTA GGG GG CGC CAG 3' | 26 | | | 5 | FAM/BHQ-1 |
| RecF3 | 5' GCA AGA GTT CAA ATA GAA AA 3' | 20 | 53.7 | | 12 | |
| RecR3 | 5' AAA GCT TTT GCA TAA ACA G 3' | 19 | 54.7 | | 13 | |
| 5BmTPK | 5' TGA GAG GAA CGA CCA TAG C 3' | 19 | 61.4 | 141 bp | 14 | |

TABLE 1-continued

Sequence of PCR primers and molecular beacon probes

| PCR primers/ Probes | Sequence | Length | Tm (C) | Size of PCR amplicon | SEQ ID No. | Fluorophore/ Quencher |
|---|---|---|---|---|---|---|
| 3BmTPK | 5' CCA TCA GGT AAA TCA CAC GAA A 3' | 22 | 61.6 | | 15 | |
| BmTPK | 5' CGC GTC GGT GTT GTT GAC CAG CGG CCG CG GAC GCG 3' | 35 | | | 16 | CAL Flour Orange 560/BHQ-1 |
| 5Aphagocyt | 5' ATG GCT ACT ACG AAG GAT 3' | 18 | 57.9 | 152 bp | 18 | |
| 3Aphagocyt | 5' CGA AGC AAC ATC TCT ACA T 3' | 19 | 58.0 | | 19 | |
| Aph1387 | 5' CGG TGC GAC AAA GAT GCC AGC ACT AAT GCG GCA CCG 3' | 36 | | | 20 | CAL Flour Red 610/ BHQ-2 |
| 5ACTA1 | 5' AGA GCA AGA GAG GTA TCC 3' | 18 | 58.0 | 104 bp | 21 | |
| 3ACTA1 | 5' CTC GTT GTA GAA GGT GTG 3' | 18 | 57.7 | | 22 | |
| ACTA1 | 5' CGC TGC CCT ATC GAG CAC GGC ATC ATC AC GCA GCG 3' | 35 | | | 23 | Quasar 670/BHQ-2 |
| Bb-RecA3 target | 5'TTATGCGCCCCCTAGGA TATCCGCCAATGC 3' | 30 | | | 2 | |
| 5BmicrotiTPK | 5' ATT ATT GTT GAA TGG GGA TAT TTG TG 3' | 26 | 64.2 | 600 bp | 24 | |
| 3BmicrotiTPK | 5' AAT AAT ATA GCT TTT CCA AAA TAT AAC TGA C 3' | 31 | 60.2 | | 25 | |
| 5ApAPH1387 | 5' ATG TAT GGT ATA GAT ATA GAG CTA AGT GA 3' | 29 | 57.8 | 1737 bp | 26 | |
| 3ApAPH1387 | 5' CTA ATA ACT TAG AAC ATC TTC ATC GTC AG 3' | 29 | 62.2 | | 27 | |
| Ba-RecA3 target | 5'TTATGCGCCCCCTAGGA TATCCACCAATGC 3' | 30 | | | 3 | |
| Bg-RecA3 target | 5'TTATTCGCCCCCTAGGA TATCCACCAATGC 3' | 30 | | | 4 | |

In the sequences of the molecular beacon probes, the nucleotides of the complementary arms are underlined, and the nucleotides of the single-strand loops are bolded.

*Borrelia burgdorferi* genomic DNA
$1.52 \times 10^6$ bp (chromosome+plasmids)
$6.0 \times 10^5$ copies/ng
2 ng $10^6$ copies

*Babesia microti* genomic DNA
$6.5 \times 10^6$ bp (chromosomes)
$1.4 \times 10^5$ copies/ng
8 ng $10^6$ copies

*Anaplasma phygocytophilum* genomic DNA
$1.47 \times 10^6$ bp (circular genome)
$6.2 \times 10^5$ copies/ng
2 ng $10^6$ copies Human HEK293 cells genomic DNA
$3.2 \times 10^9$ bp (chromosomes)
285 copies/ng
350 ng $10^5$ copies Example 1

This example demonstrates that in an assay according to this invention, molecular beacons can detect *B. burgdorferi* between 1 and $10^6$ starting copies and can quantify the starting copy number in a multiplex assay, when a human DNA sequence is also amplified and detected in real time. Real-time amplification plots of recA and ACT A1 gene target sequences in PCR assays to estimate quantities of *B. burgdorferi* (FIG. 1A) and human (FIG. 1C) DNA are shown. Human DNA (containing $10^5$ ACT A1 copies) spiked with ten-fold dilutions of *B. burgdorferi* strain N40 ranging from 1 to $10^6$ were used in the PCR assays containing both RecA3 and ACTA1 molecular beacons. Sensitivity and specificity of the detection system is indicated by the ability of RecA3 and ACTA1 molecular beacons to quantify the amplicons from both the recA and the ACT A1 genes in the same PCR assay tubes. A high coefficient of correlation ($r2=0.999$) between the PCR threshold (Ct) values and the spirochete number obtained from the standard curve (FIG. 1B) demonstrates that a multiplex assay according to this invention can be used effectively to quantify spirochete burden in infected tissues using multiplex assay system. The human DNA target sequence is not critical. We have chosen a sequence of the ACT A1 gene, but other unique human DNA targets could also be used by designing a suitable primers pair and respective molecular beacon probe.

Real-time PCR detection of recA amplicon of *B. burgdorferi* in the presence of human genomic DNA. Molecular beacons and PCR conditions were optimized for quantitative detection of *B. burgdorferi* DNA by real-time PCR (102). To use the assay for diagnosis of Lyme disease in the patients, it is important that it works in the presence of human genomic DNA. Therefore, the same quantity of human DNA (350 ng genomic DNA or $10^5$ ACT A1 copy number) was spiked with a ten-fold dilution series of genomic DNA of *B. burgdorferi*, from $10^6$ copies to $10^0$ copies. Since simultaneous detection of pathogen and host PCR products is possible using molecular beacons tagged with different fluorophores, normalization of the host DNA in patient sample is more convenient and accurate. In addition, accurate detection of host DNA in each sample ensures the quality of the DNA preparation. To evaluate this premise, primers and molecular beacons for both recA amplicon of *B. burgdorferi* and ACT A1 amplicon of human DNA were included in the starting amplification reaction mixtures, along with the *B. burgdorferi* genomic DNA and human genomic DNA.

Amplification plots of the recA gene in the PCR assays (FIG. 1A), as detected by fluorescence intensity at the end of each cycle at the annealing temperature, show that the presence of 1 to $10^6$ spirochetes is detected using the RecA3 molecular beacon. A standard curve (FIG. 1B) generated by plotting the log of the known initial copy numbers of *B. burgdorferi* versus the threshold (Ct) values from FIG. 1A indicates that the threshold cycle is inversely proportional to the number of target molecules present in the samples. A high coefficient of correlation ($r2=0.999$) between the *B. burgdorferi* copy number and the threshold cycle number (Ct) obtained from the standard curve indicates that this curve can be used to determine the quantity of spirochetes in infected mouse tissues. Since identical Ct values for ACT A1 in all samples were detected as expected, the number of copies of *B. burgdorferi* genome in the sample or the presence of human DNA does not affect sensitivity of detection of amplicon of pathogens and the host in multiplex assay (FIGS. 1A and 1C).

Example 2

Figure 2:
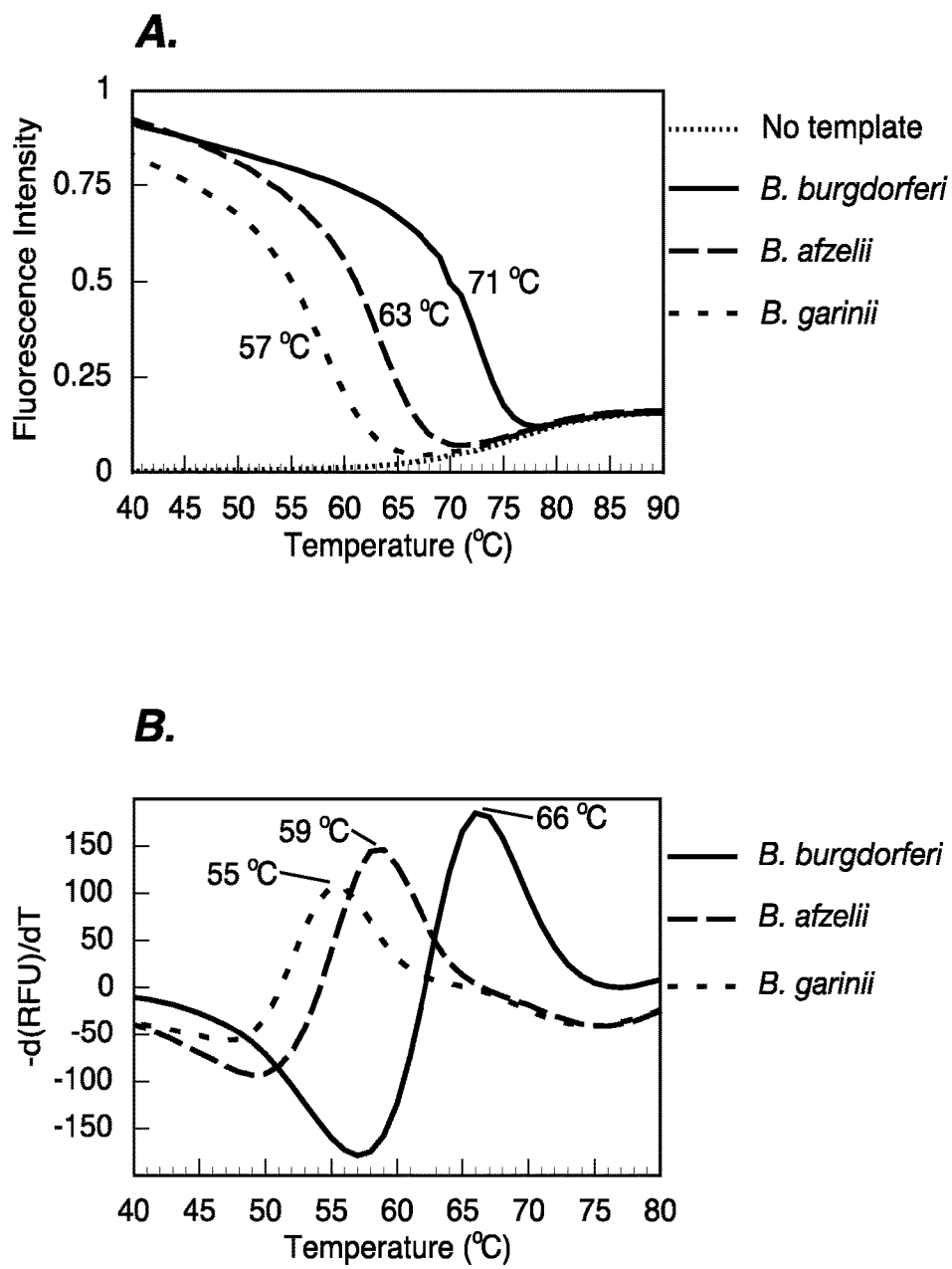

This example demonstrates that denaturation profiles of the hybrids of RecA3 molecular beacon probe with the target oligos from three *Borrelia* species can distinguish *B. burgdorferi*, *B. afzelii* and *B. garinii* (FIG. 2A). Additionally, one real-time PCR assay distinguishes three major Lyme spirochetes using post-amplification denaturation curves. Either a melting curve made by slowly increasing the reaction temperature or an annealing curve made by slowly decreasing the reaction temperature is used. Using different sets of primers and the same RecA3 molecular beacon probe, asymmetric real-time PCR amplified the fragment of recA gene from all three *Borrelia* species, and a post-PCR denaturation profile could distinguish all three spirochete species (*B. burgdorferi*, *B. afzelii*, and *B. garinii*) from one another based on the Tm of the probe-target hybrid (FIG. 2B). In the normal real-time PCR, either (i) competition between the probe and complementary strand, or (ii) secondary or tertiary structure of the target strand may decrease formation of the probe-target strand. To overcome this, non-symmetric PCR methods in which one primer or a primer pair is present in limiting amount, including LATE-PCR (Quan, P. L. et al., 2008, Antiviral Res: 79:1-5) or asymmetric PCR, was conducted such that primers for the complementary and target strand were used at 30 nM versus 1000 nM concentrations and lower amount of the molecular beacon RecA3 (12.5 ng) was included in the reaction mixture. It is noted that during PCR amplification in which real-time fluorescence intensity is monitored during the PCR annealing step (here 50° C.). as a function of cycle number (see FIG. 1A), *B. burgdorferi* gave the strongest signal, *B. afzelii* gave a somewhat weaker signal, and *B. garinii* gave the weakest signal, as shown by the curves in FIG. 2. Example 2 and FIG. 2A also indicate that the molecular beacon probe could be made perfectly complementary to either the *B. afzelii* or *B. garinii* sequence, in which case that species would have the highest Tm and give the strongest real-time signal, and *B. burgdorferi* have a lower Tm and give a weaker signal.

Differentiation of Lyme spirochete species using the denaturation profiles. Only a few single nucleotide polymorphisms (SNPs) are present in the amplicon sequences of *B. burgdorferi* sensu stricto with 100% match and corresponding *B. afzelii* and *B. microti* sequences. The loop sequence of the RecA3 molecular beacon (SEQ ID No. 5), 3' GAC CGCGGGGGATCCTATAGGCG GTC 5', is perfectly complementary to the *B. burgdorferi* 5' TTAT GCGC-CCCCTAGGATATCCGCCA ATGC 3' (SEQ ID No. 2) but less than perfectly 5' TTAT GCGCCCCTAGGATATC-CACCA ATGC 3' (SEQ ID No. 3) and less than perfectly complementary to the species *B. garinii* 5' TTAT TCGC-CCCCTAGGATATCCACCA ATGC 3' (SEQ ID No. 4).

In order to determine the melting temperatures of the molecular beacon stem and the molecular beacon probe-target hybrid, a denaturation profile analysis was carried out. Three tubes containing 200 nM molecular beacon RecA3, 3 mM MgCl2, 50 mM KCl, and 10 mM Tris-HCl (pH 8.0), in a 50-μl volume were prepared. A two-fold molar excess of an oligonucleotide that is complementary to the molecular beacon probe sequence, either *B. burgdorferi*, *B. afzelii*, or *B. garinii* sequence stated above, or only buffer were added in these tubes. The fluorescence of each solution was determined as a function of temperature. The thermal cycler was programmed to generate a denaturation curve, that is, to increase the temperature of the solutions from 40 oC to 90° C. in 1 oC steps, with each step lasting 1 min, while monitoring fluorescence during each step. The RecA3 molecular beacon was able to distinguish all three species by determination of the melting temperature (Tm) of the hybrids formed by the binding of these molecular beacons to the target sequences (FIG. 2A).

Using the asymmetric PCR, each target sequence was amplified using different primers, in this case RecF3 and RecR3 primers, and RecA3 molecular beacon (Table 1), followed by melt analysis. Taking advantage of the SNPs as discussed in the preceding paragraph, melting curve analysis identified DNA of three species. As shown in FIG. 2B, the melting-curve profiles and the Tm's (66° C., 59° C. and 55 oC) clearly identified which species was present. Viewed as denaturation profiles, one sees that as the temperature of the solution containing the hybrids is slowly raised, dissociation of the molecular beacon probes from the target strands is observed as a decrease in fluorescence intensity due to the conformational reorganization of the molecular beacons into quenched hairpin structures. The results of these experiments indicate that the three species can be distinguished from each other by simply determining the stability (as expressed by the Tm) of the resulting hybrids. These results indicate that one can use hybrid melting curves to identify more than one species of Lyme spirochete in clinical samples when each is present in 10% or more of the total spirochete population in a sample.

Example 3

This example demonstrates that in assays of this invention, molecular beacons can detect DNA from 1 and $10^6$ *Babesia microti* in a multiplex assay in the presence of human DNA and can quantify the starting copy number in a multiplex assay, when a human DNA sequence is also amplified and detected in real time. Amplification plots of BmTPK and ACT A1 genes in PCR assays using the human DNA representing $10^5$ ACT A1 copies spiked with ten-fold dilutions from 1 to $10^6$ of *B. microti* DNA copies were used to estimate quantities of *B. microti* (FIG. 3A) and human (FIG. 3C) DNA by employing both BmTPK and ACTA1 molecular beacons. The assay quantified amplicons from both the BmTPK and the ACT A1 genes in the same PCR assay tubes. A high coefficient of correlation (r2=0.993) between the Ct values and the parasite numbers obtained from the standard curve (FIG. 3B) indicates that the molecular beacons can be used effectively to quantify the parasite burden in the human infected cells using multiplex assay system using the optimized conditions.

TPK gene amplicon of *B. microti* can be detected efficiently along with human ACT A1 amplicon in the multiplex assay. Two enzymes were identified to be important in central metabolism of *B. microti* by genome sequencing of this parasite [Cornillot et al. (2012) Nucleic Acids Res 40:102-114], Lactate dehydrogenase (LDH) and TPK. Only LDH is expressed during intra-erythrocytic multiplication stage of this pathogen. Both LDH and TPK genes were cloned and initially both of the plasmid clones were used as templates for real-time PCR using SYBR green and respective molecular beacons. However, only BmTPK showed promising results. Therefore, extensive investigation was conducted using the cloned BmTPK gene only [primers 5BmicrotiTPK (SEQ ID No. 24) and 3BmicrotiTPK (SEQ ID No. 25)]. Ten-fold dilutions of plasmid containing BmTPK gene, starting with $10^6$ copies, were prepared in the human DNA (350 ng) containing $10^5$ copies of ACT A1 to use as template. Using 5BmTPK and 3BmTPK primers, BmTPK molecular beacon and PCR conditions described in the methods section, TPK and ACT A1 amplicons were detected in real time and quantified. Copy number from $10^6$ to $10^0$ of BmTPK showed steady increase in threshold cycle number (FIG. 3A). In other experiments single copy number sometimes was indistinguishable from the curve when 10 copies of TPK were present. These results are also depicted in the standard curve (FIG. 3B) and are reflected in the coefficient of correlation (r2=0.993). Overlapping ACT A1 detection curves indicate that the same concentration ($10^5$ copies) of human DNA included in different tubes for TPK-containing plasmids dilutions had the same threshold cycle and so were accurately quantitated. Thus, it is expected that 10 copies of TPK will be detected consistently in this assay.

Example 4

This example demonstrates that in assays of this invention, molecular beacons can detect DNA from 1 and $10^6$ *Anaplasma phagocytophilum* in a multiplex assay in the presence of human DNA and can quantify the starting copy number in a multiplex assay, when a human DNA sequence is also amplified and detected in real time. Amplification plots of APH1387 and ACT A1 genes in PCR assays using the human DNA representing $10^5$ ACT A1 copies spiked with ten-fold dilutions from 1 to $10^6$ plasmid copies containing APH1387 were used to estimate quantities of *A. phagocytophilum* (FIG. 4A) and human (FIG. 4C) DNA by employing both Aph1387 and ACT A1 molecular beacons. The assay quantified amplicons from both the APH1387 and the ACT A1 genes in the same PCR assay tubes. A high coefficient of correlation (r2=0.985) between the Ct values and the parasite numbers obtained from the standard curve (FIG. 4B) indicates that the molecular beacons can quantify burden of this intracellular pathogen in the human infected cells using multiplex assay system using the standardized conditions in a sensitive and specific manner.

Specific detection of APH1387 amplicon in the presence of human DNA using molecular beacon probes in multiplex assay. *A. phagocytophilum* is an obligate intracellular pathogen that multiplies within a vacuole inside the host cells that avoids fusion with lysosome. APH1387 of *A. phagocytophilum* was identified as the first protein that localizes to the vacuolar membrane containing this pathogen [Huang et al. (2010) J Microbiol 48:877-880]. Since the gene is uniquely present in *A. phagocytophilum* and is highly conserved in various strains, we selected it to use for detection of this bacterium by rt-PCR and first amplified it using 5ApAPH1387 and 3ApAPH1387 primers (SEQ ID Nos. 26 and 27). By using the strategy used for TPK gene containing plasmid for *B. microti* as described above, APH1387 containing plasmid was diluted in human DNA, and PCR was conducted using 5Aphagocyt and 3Aphagocyt primers and Aph1387 molecular beacon. Primers for human ACT A1 amplicon and ACTA1 molecular beacon were also included in the reaction mixture. Conditions for PCR were identical to those used for Lyme spirochetes recA and *B. microti* TPK gene amplifications. Real-time fluorescence readings of the Aph1387 probe are presented in FIG. 4A. Real-time readings of the ActA1 probe are presented in FIG. 4C. Because the curves for $10^1$ copies of target and $10^0$ copies of target were not well separated, the APH1387 detection limit was judged to be close to 10 (FIG. 4A), similar to that for the TPK detection sensitivity of *B. microti* observed sometimes and not close to 1 consistently as observed for recA amplicon of Lyme spirochetes. Again, the results were reflected in the standard curve and coefficient of correlation of 0.985 (FIG. 4B). Sensitivity of detection of human ACT A1 amplicon was maintained similar to the multiplex assays described for recA and BmTPK amplicons above.

Example 5

This example describes a quadruplex assay according to this invention. Example 5 demonstrates that inclusion of three tick-borne pathogens in the presence of human DNA in a single quadruplex assay does not affect the sensitivity of their detection. Conditions for a quadruplex PCR assay were optimized such that eight primers (four pairs) and four different molecular beacons for respective amplicons were present in the same tube along with the other reagents required for PCR. Sensitivity of detection of two bacterial pathogens, extracellular spirochete *B. burgdorferi* (FIG. 5A) and obligate intracellular pathogen *A. phagocytophilum* (FIG. 5C), along with the intracellular parasite, *B. microti* (FIG. 5B), was not affected in this quadruplex assay, demonstrating that the assay can be extended for simultaneous diagnosis of all three tick-borne pathogens in patients, especially in endemic regions. Detection of the ACT A1 amplicon in the same reaction will offer as control for human DNA (FIG. 5D) and quality of DNA preparation when the patient samples will be used for diagnosis of the infecting organism. Since most real time PCR machines can now detect five fluorophore simultaneously, this assay can be expanded to include another tick-borne pathogen, such as, Powassan virus, which is emerging in Hudson Valley ticks and cause rather fatal disease.

Optimization of conditions for simultaneous detection of recA of Lyme spirochetes, TPK of *B. microti* and APH1387 amplicon of *A. phagocytophilum*. Since Lyme disease is the most prevalent tick-borne disease in the USA and it is also widespread in Europe, and because emerging pathogens *Babesia* species and *A phagocytophilum* are found to be co-infecting the same species of the ticks, it is very likely that a few cases of co-infections in humans will increase steadily in the near future. Therefore, development of a single multiplex real-time PCR assay for detection of all three tick-borne pathogens simultaneously in the patient samples in a sensitive and specific manner is expediently warranted. To achieve this goal, experimental conditions were standardized such that genomic DNA of *B. burgdorferi* and plasmids containing BmTPK and APH1387 genes were serially diluted in human DNA containing $10^5$ copies of ACT A1 gene. The quadruplex reaction mixture was amplified by PCR, with probe readings in real time. FIG. 5A shows the results for varying concentrations of the recA target, FIG. 5B shows the results with varying concentrations of the BmTPK target, FIG. 5C shows the results with varying concentrations of the Aph1387 target, and FIG. 5D shows the results for the ACT A1 target ($10^5$ copies). By increasing the concentration of molecular beacons in the quadruplex assay mixture, we were able to improve the sensitivity of detection of both *B. microti* TPK and *A. phagocytophilum* APH1387 amplicons such that curve for 1 copy was clearly distinguishable from 10 copies (FIGS. 5B and 5C). Amplicons from all three pathogens along with the control human ACT A1 gene amplicon were detected in one assay. Sensitivity of detection of any of the three pathogens amplicons was not affected in the assay.

Example 6

This example demonstrates that in a multiples assay an excess of *B. burgdorferi* genomic DNA does not affect sensitivity of detection of *A. phagocytophilum* and *B. microti* genomic DNA. Genomic DNA of *B. burgdorferi* representing $10^6$ copies of recA gene mixed with *A. phagocytophilum* and *B. microti* genomic DNA each reflecting $10^3$ (FIG. 6) copies of BmTPK and APH1387 genes, respectively were used as template in the multiplex PCR amplification assay. Sensitivity and specificity of detection of BmTPK and APH1387 amplicons was retained in a $10^3$-fold excess of recA gene copies in the reaction mixture.

Sensitivity of detection of emerging pathogens *B. microti* and *A. phagocytophilum* DNA is retained in the presence of excess of *B. burgdorferi* DNA. Even though cloned genes of both of these pathogens in plasmids could be detected and quantitated when present individually and together with *B. burgdorferi*, it is essential to determine if the sensitivity is maintained when their genomic DNA is used as template. In addition, quantities of these emerging pathogens may vary in the patient samples. Therefore, the sensitivity of the assay for detection of *B. microti* and *A. phagocytophilum* in excess of *B. burgdorferi* DNA was assessed. *B. burgdorferi* genomic DNA/recA copy number ($10^6$) along with genomic DNA equivalent to $10^3$ copies of BmTPK and APH1387 each was used. Real-time probe readings are presented in FIG. 6. As shown by this Figure, the accuracy and sensitivity of detection of *B. microti* and *A. phagocytophilum* was not affected by $10^3$-fold excess of *B. burgdorferi* genomic DNA, validating the applicability of multiplex assays according to this invention for diagnosis of all three tick-borne infections even if Lyme spirochetes are present in excess in the sample, such as in synovial fluid or skin biopsy samples.

Example 7

This example demonstrates that in a multiplex assay with an excessive DNA quantity, in this case a one hundred-fold excess, of *A. phagocytophilum* and *B. microti* genomic DNA relative to the *B. burgdorferi* DNA does not affect sensitivity of detection of spirochetal recA amplicon. Genomic DNA of *B. burgdorferi* representing 10 copies of recA gene mixed with *A. phagocytophilum* and *B. microti* genomic DNA each reflecting $10^3$ copies of BmTPK and APH1387 genes, respectively were used as template in the multiplex assay. Real-time fluorescence curves for the three probes are shown in FIG. 7. As FIG. 7 demonstrates, sensitivity and specificity of detection of recA amplicon was not affected by the excess of *A. phagocytophilum* and *B. microti* genomic DNA in the reaction mixture. Such a scenario is expected in nature, particularly in the blood samples of patients co-infected with these tick-borne pathogens.

*B. burgdorferi* can be accurately detected even in the 100-fold excess of *B. microti* and *A. phagocytophilum* genomic DNA. Blood is primarily used as a conduit by Lyme spirochetes to disseminate to various tissues such that usually only a few *B. burgdorferi* are present in the blood at any given time. Therefore, it is likely that blood-borne pathogens *A. phagocytophilum* and *B. microti* could be present in higher numbers in blood during co-infection with *B. burgdorferi*. To determine whether detection of *B. burgdorferi* could be affected by the presence of higher levels of parasitemia by *B. microti* and/or bacteremia by *A. phagocytophilum*, genomic DNA of all three pathogens were mixed such that the copy number of BmTPK and APH1387 ($10^3$) was 100-fold of that of recA of *B. burgdorferi* [Bakken (2002) J Contin Educ Health Prof 22:131-141] in a triplex PCR amplification reaction containing primers and a probe for each of the three genes. Real-time curves (fluorescence intensity versus PCR cycle number) from each of the three probes are shown in FIG. 7. Ten copies of *B. burgdorferi* recA per one thousand copies of BmTPK and APH1387 were consistently detected in a multiplex assay (FIG. 7). These results demonstrate that irrespective of the levels of each pathogen relative to the other two pathogens, multiplex rt-PCR assays according to this invention accurately detect each pathogen in the mixture.

Example 8

This example describes a hexaplex assay according to this invention. This example demonstrates that the assay can simultaneously in real time detect five tick-borne pathogens: three species of Lyme disease spirochetes (*B. burgdorferi*, *B. afzelii*, and *B. garinii*), the protozoan pathogen *B. microti*, and the intracellular bacterial pathogen *A. phagocytophilum*, as well as detecting the presence of human ACT A1 DNA, in a single assay.

Conditions for the hexaplex PCR assay are optimized in the manner described above, such that four pairs of primers and six differently colored molecular beacons are included in the same tube, along with the other reagents required for PCR. One pair of primers (listed in Table 1) enables the amplification of a region of *Borrelia* DNA that is common to all three *Borrelia* species, and three different molecular beacons are present, each specific for a different *Borrelia* species, and each labeled with a differently colored fluorophore. The three other pairs of primers (also listed in Table 1) enable the amplification of a region of *A. phagocytophilum* DNA, a region of *Borrelia microti* (or other *Babesia* species) DNA, and a region of the human ACT A1 gene, and three additional molecular beacons are present, each specific for one of the three resulting amplicons, and each labeled with a differently colored fluorophore. The real-time PCR reaction and detection of the fluorescence from each of the six molecular beacons is carried out in the manner described above in an instrument that is able to distinguish at least six different colors. All five pathogens, along with the control human ACT A1 gene, are therefore detected and quantitated in a single real-time PCR assay, The optimized multiplex assays of the present invention accurately detect and quantify a single spirochete recA gene copy spiked in the human DNA. The presence of high concentrations of human genomic DNA (containing $10^5$ copies of ACT A1 gene) did not affect accuracy of the assay (FIG. 1) as also shown by almost perfect coefficient of correlation (r2=0.999) between threshold cycle and copy number of *B. burgdorferi* DNA. Consistency of detection of ACT A1 gene amplicon in all tubes indicated that each molecular beacon probe, for *B. burgdorferi* and ACTA1, tagged with a different fluorophore can accurately detect respective amplicons, and the sensitivity of the assay is not affected due to interference from the presence of other pathogens DNA. As proof of the principle, specific oligonucleotides for *B. burgdorferi* sensu stricto, *B. afzelii* and *B. garinii* sequence were designed which show the presence of SNPs in the probe-binding region. Using a single molecular beacon, three species oligos were discriminated by determining the Tm from the denaturation curves (FIG. 2). Real-time PCR using the hbb gene and reverse complementary 3'-fluorescein-labeled probe designed against the forward strand of amplicon was able to distinguish different *Borrelia* species by Tm determination [Ferdin et al. (2010) J Microbiol Meth 82:115-119]. The methods of the present invention accurately detect Lyme spirochetes and also distinguish three different species of Lyme spirochetes. This assay can be easily extended to include other emerging *Borrelia* species implicated in Lyme disease, such as *B. miyamotoi*, which appears to cause more severe illness in humans [Krause et al. (2013) New England J Med 368:291-293]. Such discrimination is important to determine accurate association between specific chronic Lyme disease symptoms with particular *Borrelia* species.

Figure 5:
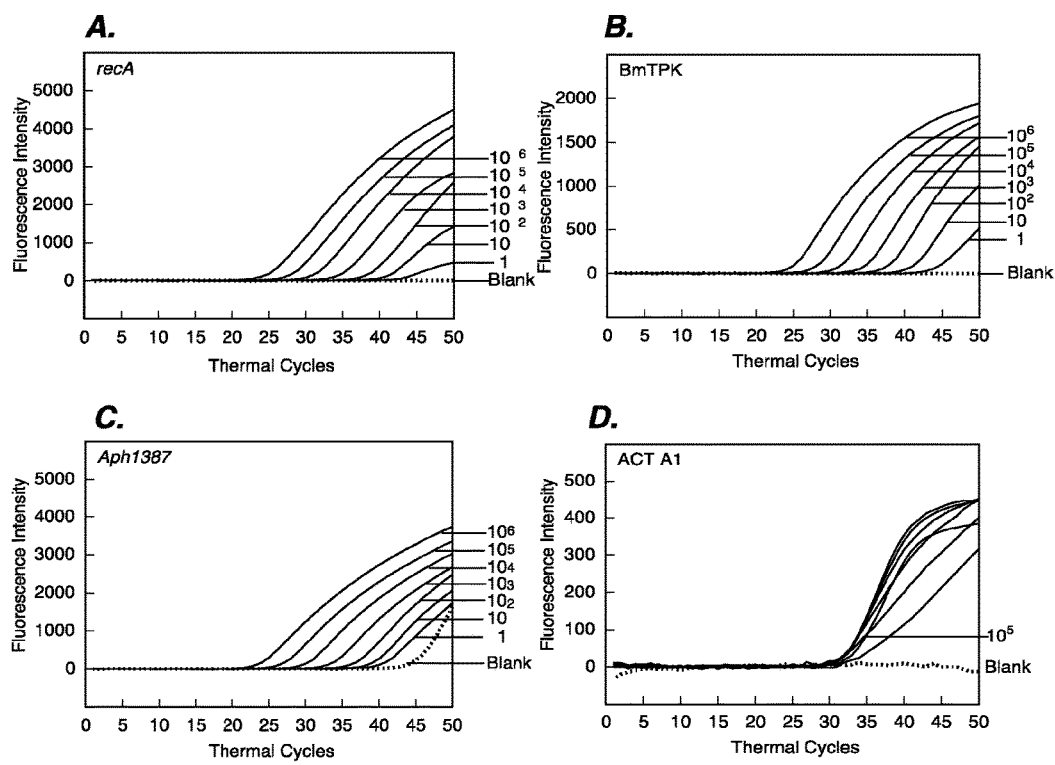

The best time to develop an efficient diagnostic test is when infections by a particular organism start emerging among human or animal populations, environment or in the vectors. Since infections of ticks by two tick-borne pathogens, *A. phagocytophilum* and *Babesia* species, have been increasing in both Europe and the USA, and because the cases by these emerging pathogens are also being reported in higher numbers on both continents [Beugnet and Marie (2009) Veterinary Parasitology 163:298-305; Dantas-Torres et al. (2012) Trends in Parasitology 28:437-446; Graham et al. (2011) Pediatr Emerg Care 27:141-147, quiz 148-50; Heyman et al. (2010) Expert Rev Anti Infect Ther 8:33-50; and Socolovschi et al. (2009) Parasitology 16:259-273], the present invention was expanded to include detection of these two pathogens. Indeed, co-infections with these tick-borne pathogens have started appearing in patients, resulting in exhibition of more severe illnesses [Horowitz et al. (2013) Clinical infectious diseases 56:93-99; and Wormser et al. (2013) J Clin Microbiol 51:954-958]. Optimized conditions for detecting each emerging pathogen, using the *B. microti* and *A. phagocytophilum* genes BmTPK and APH1387, respectively, with human ACT A1 individually (FIGS. 3 and 4), worked well, even in a quadrupex assay in which serially diluted genomic DNA of *B. burgdorferi* and human could be accurately detected in addition to BmTPK and APH1387 containing plasmid DNA (FIG. 5). Moreover, this test detected as few as $10^3$ copies of both APH1387 and BmTPK in mixed genomic DNA in the presence of an excess ($10^3$-fold copy number) of *B. burgdorferi* DNA, confirming the sensitivity and accuracy of the assay. The methods of the present invention demonstrate an efficient and quick assay to detect individual pathogens, such as *B. microti* in blood bank samples using the approach shown in FIG. 3. Co-infections with two or three pathogens in the endemic regions for these tick-borne diseases using the triplex or quadruplex assay are also diagnosed according to the methods of the present invention (FIGS. 5, 6, and 7). The present invention describes novel assays for the sensitive detection of three tick-borne pathogens simultaneously. These assays can be easily adapted for the patient samples in the future with little modification if needed.

The foregoing examples and description of the preferred embodiments should be interpreted as illustrating, rather than as limiting the present invention as defined in the specification. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. A kit for diagnosing a tick-borne disease, the kit comprising at least two of the following:
   a. a pair of *Borrelia* primers for a recA gene sequence of Lyme disease-causing *Borrelia*, having the respective sequences of SEQ ID Nos: 12 and 13; and a *Borrelia*-specific molecular beacon probe capable of distinguishing among *B. burgdorferi*, *B. afzelii*, and *B. garinii* having the sequence of SEQ ID No: 5;
   b. a pair of *Babesia* primers for a conserved *B. microti* thiamine pyrophosphokinase (BmTPK) gene sequence having the respective sequences of SEQ ID Nos: 14 and 15 or of SEQ ID Nos: 24 and 25 and a *Babesia*-specific molecular beacon probe having the sequence of SEQ ID No: 16; and
   c. a pair of *Anaplasma* primers for a conserved *Anaplasma phagocytophilum* (APH) 1387 gene sequence of *A. phagocytophilum* having the respective sequences of SEQ ID Nos: 18 and 19, or of SEQ ID Nos: 26, and 27 and an *Anaplasma*-specific molecular beacon probe having the sequence of SEQ ID No: 20,
   wherein each of said primer pairs amplifies an amplicon that is 70-300 base pairs in length, wherein primer annealing is performed at a temperature below or equal to a primer-extension temperature during an amplification reaction, and wherein each molecular beacon probe is labeled with a spectrally distinguishable fluorescent or luminescent signaling moiety.

2. The kit of claim 1 further comprising a pair of ACT A1 primers having the sequences of SEQ ID Nos. 21 and 22 for a human DNA ACT A1 gene sequence and an ACT A1 molecular beacon probe having the sequence of SEQ ID No. 23.

3. The kit of claim 1 further comprising one or more reagents selected from the group consisting of a buffer, a DNA polymerase, and nucleotides.

* * * * *